US012539379B2

(12) United States Patent
Gutmark-Little et al.

(10) Patent No.: US 12,539,379 B2
(45) Date of Patent: Feb. 3, 2026

(54) DEVICE FOR UNBLOCKING AND REMOVING SECRETIONS FROM AIRWAYS

(71) Applicants: Children's Hospital Medical Center, Cincinnati, OH (US); University of Cincinnati, Cincinnati, OH (US); B.G. Negev Technologies and Applications Ltd., at Ben Gurion University, Beer-Sheva (IL); Mor Research Applications Ltd., Tel Aviv (IL)

(72) Inventors: Iris Gutmark-Little, Cincinnati, OH (US); Ephraim Gutmark, Cincinnati, OH (US); Yuval Cavari, Beer-Sheva (IL); David Katoshevski, Beer-Sheva (IL)

(73) Assignees: Children's Hospital Medical Center, Cincinnati, OH (US); University of Cincinnati, Cincinnati, OH (US); B.G. Negev Technologies and Application Ltd., at Ben Gurion University, Beer-Sheva (IL)

( * ) Notice: Subject to any disclaimer, the term of this patent is extended or adjusted under 35 U.S.C. 154(b) by 1030 days.

(21) Appl. No.: 16/961,622

(22) PCT Filed: Jan. 11, 2019

(86) PCT No.: PCT/US2019/013387
§ 371 (c)(1),
(2) Date: Jul. 10, 2020

(87) PCT Pub. No.: WO2019/140333
PCT Pub. Date: Jul. 18, 2019

(65) Prior Publication Data

US 2020/0338288 A1 Oct. 29, 2020

Related U.S. Application Data

(60) Provisional application No. 62/616,804, filed on Jan. 12, 2018.

(51) Int. Cl.
*A61M 16/00* (2006.01)
*A61M 16/20* (2006.01)

(52) U.S. Cl.
CPC ...... *A61M 16/0006* (2014.02); *A61M 16/202* (2014.02); *A61M 2016/0027* (2013.01); (Continued)

(58) Field of Classification Search
CPC .... A61M 16/00-0006; A61M 16/0051; A61M 16/0057-0084; A61M 16/0096; A61M 16/20-202; A61M 2016/0027
See application file for complete search history.

(56) References Cited

U.S. PATENT DOCUMENTS 2,918,917 A 12/1959 Emerson
4,602,644 A 7/1986 DiBenedetto et al.
(Continued)

FOREIGN PATENT DOCUMENTS

CN 202236141 U 5/2012
CN 203829278 U 9/2014
(Continued)

OTHER PUBLICATIONS

Barrett, Brooks, Boitano and Barman; Ganong's Review of Medical Physiology, 23rd Edition (2010), 10 pages.
(Continued)

*Primary Examiner* — Rachel T Sippel
(74) *Attorney, Agent, or Firm* — Bose McKinney & Evans LLP

(57) ABSTRACT

A device for unblocking and removing secretions from airways, including small airways, by applying oscillated air flow and acoustic vibrations, illustratively according to preprogrammed protocol that defines at least one of frequency, waveform, pressure amplitude, and oscillation duration. In an illustrative embodiment, the device applies a
(Continued)

combination of air flow oscillations and acoustic waves to facilitate detachment of mucus from airway walls by matching the resonance of specific airway sections and mucus, amplifying the effect. For optimization, an algorithm illustratively matches the required frequencies, amplitudes, duty cycle, and/or relative phases to specific patient and secretion characteristics.

37 Claims, 24 Drawing Sheets

(52) U.S. Cl.
CPC . *A61M 2205/505* (2013.01); *A61M 2205/581* (2013.01); *A61M 2205/583* (2013.01); *A61M 2205/8206* (2013.01); *A61M 2209/02* (2013.01); *A61M 2230/46* (2013.01)

(56) References Cited

U.S. PATENT DOCUMENTS

| | | | | |
|---|---|---|---|---|
| 5,307,794 | A | 5/1994 | Rauterkus et al. | |
| 5,611,335 | A | 3/1997 | Makhoul et al. | |
| 5,829,429 | A | 11/1998 | Hughes | |
| 5,893,361 | A | 4/1999 | Hughes | |
| 5,921,232 | A | 7/1999 | Yokoi et al. | |
| 6,152,130 | A | 11/2000 | Abrams et al. | |
| 6,457,654 | B1 | 10/2002 | Glezer et al. | |
| 7,478,634 | B2 | 1/2009 | Jam | |
| 7,617,821 | B2 | 11/2009 | Hughes | |
| 8,082,920 | B2 | 12/2011 | Hughes | |
| 8,347,883 | B2 | 1/2013 | Bird | |
| 8,443,796 | B2 | 5/2013 | Hughes | |
| 8,539,952 | B2 | 9/2013 | Carbone et al. | |
| 8,702,379 | B2 | 4/2014 | Frater et al. | |
| 8,776,790 | B2 | 7/2014 | Gentner et al. | |
| 8,875,705 | B2 | 11/2014 | Avni | |
| 8,967,143 | B2 | 3/2015 | Gutmark et al. | |
| 9,114,224 | B2 | 8/2015 | Avni | |
| 9,504,796 | B2 | 11/2016 | Perlman | |
| 10,166,350 | B2 | 1/2019 | Kaufmann | |
| 10,173,019 | B2 | 1/2019 | Kaufmann et al. | |
| 10,646,668 | B2 | 5/2020 | Avni | |
| 2002/0014235 | A1 | 2/2002 | Rogers et al. | |
| 2004/0069304 | A1* | 4/2004 | Jam | A61M 16/021 128/204.23 |
| 2008/0156319 | A1 | 7/2008 | Avni | |
| 2009/0098015 | A1 | 4/2009 | Bhardwaj | |
| 2009/0126731 | A1 | 5/2009 | Dunsmore et al. | |
| 2010/0125227 | A1 | 5/2010 | Bird | |
| 2012/0095374 | A1 | 4/2012 | Hughes | |
| 2012/0103337 | A1 | 5/2012 | Avni | |
| 2012/0190981 | A1 | 7/2012 | Harris | |
| 2012/0199127 | A1 | 8/2012 | Garde et al. | |
| 2013/0092167 | A1 | 4/2013 | Perlman | |
| 2013/0186399 | A1 | 7/2013 | Gutmark et al. | |
| 2014/0107569 | A1 | 4/2014 | Fischer | |
| 2014/0190481 | A1 | 7/2014 | Jam | |
| 2016/0121062 | A1 | 5/2016 | Davenport et al. | |
| 2016/0339191 | A1* | 11/2016 | Kaczka | A61M 16/0006 |
| 2017/0020776 | A1* | 1/2017 | Khasawneh | A61B 5/486 |
| 2017/0079733 | A1* | 3/2017 | Darrah | A61B 5/0022 |
| 2018/0071469 | A1* | 3/2018 | Oldfield | A61M 16/0672 |
| 2018/0085541 | A1* | 3/2018 | Ye | A61M 16/024 |
| 2019/0262559 | A1 | 8/2019 | Bogan et al. | |

FOREIGN PATENT DOCUMENTS

| | | | |
|---|---|---|---|
| CN | 204766943 | U | 11/2015 |
| EP | 2 349 422 | B1 | 5/2017 |
| EP | 2 506 909 | B1 | 10/2018 |
| FR | 2 742 056 | | 6/1997 |
| FR | 2 835 435 | | 8/2003 |
| GB | 2 133 664 | B | 8/1984 |
| GB | 2 196 858 | A | 5/1988 |
| RU | 2082372 | C1 | 6/1997 |
| WO | WO 03/105937 | A1 | 12/2003 |
| WO | WO 2004/020029 | A1 | 3/2004 |
| WO | WO 2006/129304 | A2 | 12/2006 |
| WO | WO 2010/038233 | A1 | 4/2010 |
| WO | WO 2011/067763 | A1 | 6/2011 |
| WO | WO 2015/017416 | A1 | 2/2015 |
| WO | WO 2015/136529 | A1 | 9/2015 |
| WO | WO 2015/186124 | A1 | 12/2015 |
| WO | 2016157104 | A1 | 10/2016 |
| WO | 2016159889 | A1 | 10/2016 |
| WO | 2016210266 | A1 | 12/2016 |
| WO | WO 2017/089369 | A1 | 6/2017 |
| WO | WO 2017/187390 | A1 | 11/2017 |
| WO | WO 2017/187390 | A9 | 11/2017 |
| WO | WO 2018/026549 | A1 | 2/2018 |
| WO | 2019140333 | A1 | 7/2019 |
| WO | WO 2020/225817 | A1 | 11/2020 |

OTHER PUBLICATIONS

Miller, Cohen, Eriksson, Fleisher, Wiener-Kronish and Young, Miller's Anesthesia, 8th Edition (2015), 20 pages.

Fernandez-Restrepo, Shaffer, Amalakuhan, Restrepo, Peters and Restrepo; Effects of intrapulmonary percussive ventilation on airway mucus clearance: A bench model; World Journal of Critical Care Medicine; World J Crit Care Med; Aug. 4, 2017; 6(3): 164-171; 9 pages.

International Search Report and Written Opinion mailed Apr. 12, 2019, from the International Search Authority in priority application No. PCT/US2019/013387, 17 pgs.

George et al., Increase in mucociliary clearance in normal man induced by oral high frequency oscillation, Thorax (1985), vol. 40, pp. 433-437, downloaded from http://thorax.bmj.com on Jan. 23, 2019.

Hall et al., Textbook of Medical Physiology, Twelfth Edition, ISBN: 978-1-4160-4574-8, downloaded from http://www.us.elsevierhealth.com/product.jsp?isbn=9781416045748&elscal=doodys&elsca2=PDF&elsca3=Hall9781416045748&elsca4=frontmatter, Copyright © 2011, 2006, 2000, 1996, 1986, 1981, 1976, 1966, 1961 and 1956, 20 pgs.

Flint et al., Cummings Otolaryngology Head & Neck Surgery, ISBN: 978-0-323-05283-2, downloaded from http://www.us.elsevierhealth.com/product.jsp?isbn=9780323052832&elscal=doodys&elsca2=PDF&elsca3=Flint9780323052832&elsca4-frontmatter, Copyright © 2010, 2005, 1998, 1993 and 1986, 42 pgs.

Fernandez-Restrepo et al., Effects of intrapulmonary percussive ventilation on airway mucus clearance: A bench model, World J Crit Care Med, Aug. 4, 2017, vol. 6(3), pp. 164-171.

Chatburn, High-Frequency Assisted Airway Clearance, Respiratory Care, Sep. 2007, vol. 52, No. 9, pp. 1224-1237.

Fahy et al., Airway Mucus Function and Dysfunction, The New England Journal of Medicine, pp. 2233-2247, Copyright © by Massachusetts Medical Society, Jan. 23, 2019, 15 pgs.

Bonser, et al., Epithelial tethering of MUC5AC-rich mucus impairs mucociliary transport in asthma, The Journal of Clinical Investigation, vol. 126, No. 6, Jun. 2016, pp. 2367-2371.

Andrews et al., Nonpharmacologic Airway Clearance Techniques in Hospitalized Patients: A systematic review, Respiratory Care Paper in Press, Published on Nov. 12, 2013 as DOI: 10.4187/respcare.02704, Copyright © 2013 by Daedalus Enterprises, 76 pgs.

ASL 5000 Breathing Simulator, Respiratory Simulation Specialists, retrieved on Dec. 7, 2017, 5 pgs.

Zahm et al., Role of simulated repetitive coughing in mucus clearance, Eur Respir J, 1991, vol. 4, pp. 311-315.

Vargas et al., Intrapulmonary percussive ventilation in acute exacerbations of COPD patients with mild respiratory acidosis: a randomized controlled trial [ISRCTN17802078], Critical Care, vol. 9, No. 4, pp. R382-R389, available online at http://ccforum.com/content/9/4 /R382, published Jun. 1, 2005, 8 pgs.

Walsh et al., Pediatric Airway Maintenance and Clearance in the Acute Care Setting: How to Stay Out of Trouble, Respiratory Care, Sep. 2011, vol. 56, No. 9, pp. 1424-1444.

(56) References Cited

OTHER PUBLICATIONS

Schans et al., Physiotherapy and bronchial mucus transport, European Respiratory Journal, 1999, vol. 13, pp. 1477-1486.
Sperling, Sound and Vibration Damping with Polymers, ACS Symposium Series, American Chemical Society, Washington, DC, 1990, downloaded on Jan. 23, 2019 from https://pubs.acs.org/sharingguidelines, pp. 5-22.
Toussaint, et al., Effect of Intrapulmonary Percussive Ventilation on Mucus Clearance in Duchenne Muscular Dystrophy Patients: A Preliminary Report, Respiratory Care, Oct. 2003, vol. 48, No. 10, pp. 940-947.
Rogers, Physiology of Airway Mucus Secretion and Pathophysiology of Hypersecretion, Respiratory Care, Sep. 2007, vol. 52, No. 9, pp. 1134-1149.
Rubin, Secretion properties, clearance, and therapy in airway disease, Translational Respiratory Medicine, 2014, 2:6, downloaded from http://www.transrespmed.com/content/2/1/6, pp. 1-7.
Reardon et al., Intrapulmonary Percussive Ventilation vs Incentive Spirometry for Children With Neuromuscular Disease, Arch Pediatrics Adolescence Med, Jun. 2005, vol. 159, pp. 526-531, Copyright © 2005 by American Medical Association.
Ramos et al., Clinical issues of mucus accumulation in COPD, International Journal of COPD, 2014, vol. 9, pp. 139-150.
Kim, Lung mucus: a clinician's view, European Respiratory Journal, 1997, vol. 10, pp. 1914-1917.
Michigan Instruments, Dual Adult Test Lung Simulator, retrieved on Dec. 7, 2017 from https://www.michiganinstruments.com/training-test-lung-simulators/dual-adult-training-test-lung, 3 pgs.
Bronchiectasis Toolbox, Positive Expiratory Pressure Therapy, retrieved on Dec. 7, 2017 from http://bronchiectasis.com.au/physiotherapy/techniquest/positive-expiratory-pressure-therapy, 11, pgs.
Yoo et al., Pilot Study: Understanding the Effects of Voicing Intervention on HFCC Therapy in People with Cystic Fibrosis, Journal of Voice, vol. 23, No. 4, 2009, 6 pages.

* cited by examiner

EXHIBIT E
Upstream and Downstream Pressure Measurements
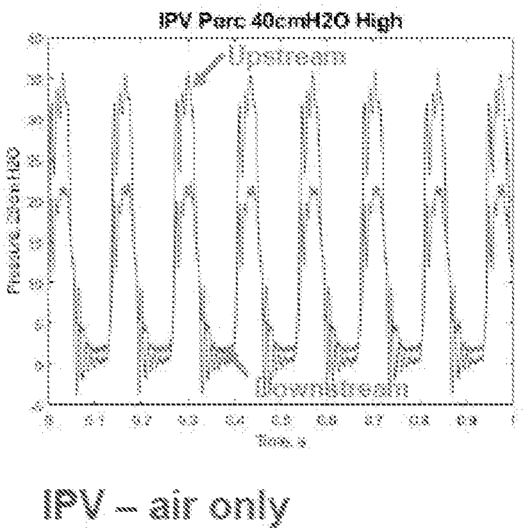
(a) Air Flow Only Device
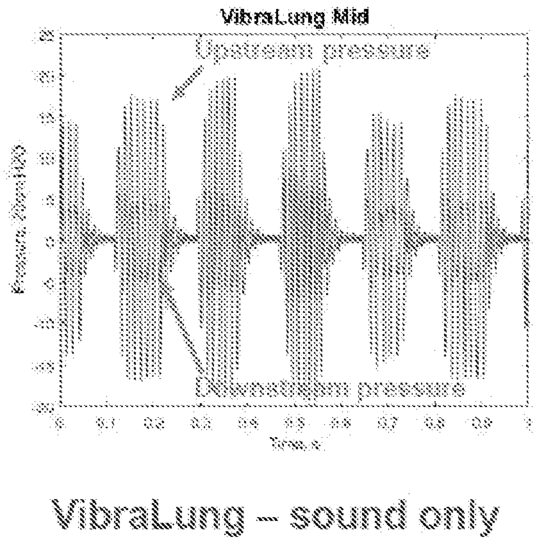
(b) Acoustic Only Device

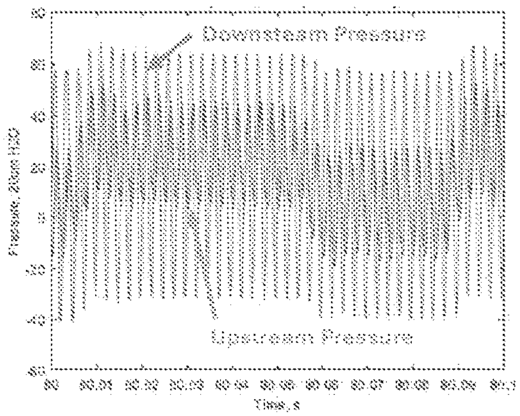
(c) The Inventive Device
Figure 3. Pressure traces comparing proximal (blue) and distal (orange) pressure sensor readings with (a) air pulse only, (b) acoustic only and (c) acoustic + air pulse modes.

○ 300 bpm, 300 Hz
□ 300 bpm, 400 Hz
☆ 400 bpm, 300 Hz
● 400 bpm, 400 Hz
△ 300 bpm, 0 Hz
◇ 400 bpm, 0 Hz
FIG. 15A
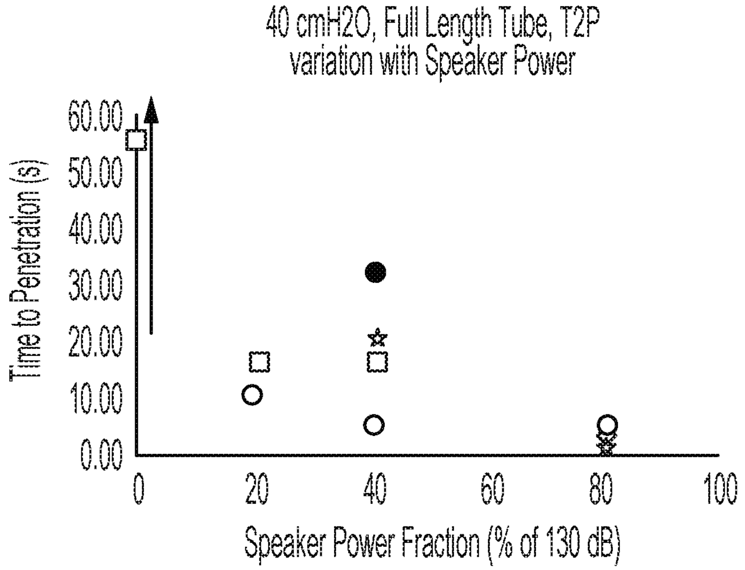
FIG. 15B
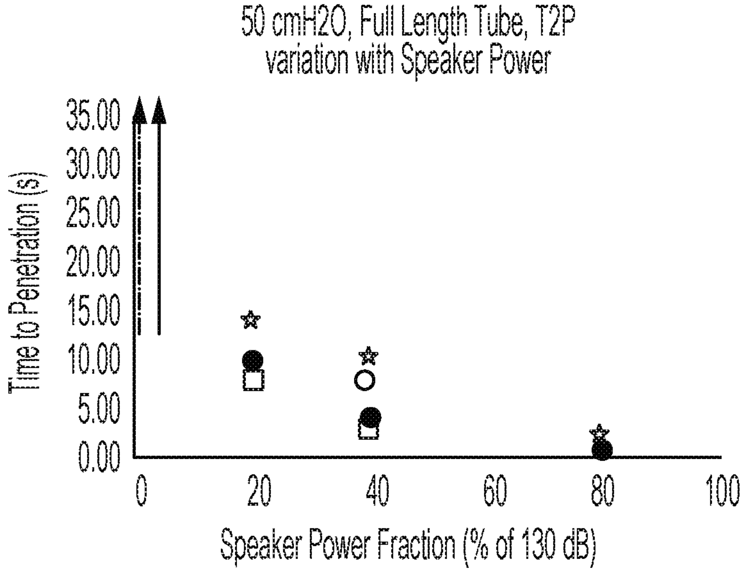
FIG. 15C

DEVICE FOR UNBLOCKING AND REMOVING SECRETIONS FROM AIRWAYS

CROSS-REFERENCE TO RELATED APPLICATION

The present application claims priority to U.S. Provisional Patent Application Ser. No. 62/616,804, filed Jan. 12, 2018, the disclosure of which is expressly incorporated herein by reference.

GOVERNMENT SUPPORT CLAUSE

This invention was made with government support under HL119810 awarded by the National Institutes of Health. The Government has certain rights in the invention.

BACKGROUND AND SUMMARY OF THE DISCLOSURE

The present disclosure relates to devices that assist in breaking up or dislodging accumulated secretions from airways and, more particularly, to such devices utilized in the treatment of respiratory disorders.

Respiratory inhalers are often used in the medical field to treat a variety of upper respiratory illnesses and diseases. Some upper respiratory diseases may be chronic and require lifetime therapy. Devices are known in the art to facilitate the removal of mucus and other solids and fluids from airways, especially for patients with such lifelong, chronic illnesses. However, conventional secretion removal devices may be inefficient and not well-suited for small airways.

For example, acute bronchiolitis is a common disease in infants often caused by viral pathogens and characterized by thick, inflammatory secretions blocking and clogging the infant's small airways. This may lead to respiratory distress or respiratory failure, necessitating mechanical ventilation. Some treatment devices known in the art can worsen the infant's condition, while others are not effective in clearing small airways. Similarly, patients with Chronic Obstructive Pulmonary Disease ("COPD") suffer from the narrowing of small airways, but available treatments typically do not effectively treat the small airways. This makes the functional capacity and perceived well-being of COPD patients sub-optimal. Thus, a need exists for a non-invasive device for treating, and more particularly for unblocking and removing, secretions in airways, particularly small airways, of patients.

The device and method of the present disclosure is configured to apply a combination of air flow oscillations and acoustic waves to facilitate removal of mucus by breaking down or deagglomerating mucus chunks, detaching them from the airway wall, and facilitating clearance. Illustratively, the mucus disintegration and detachment from the airway wall is accomplished by a combination of oscillating air flow and acoustic pulses that are configured to match the resonance of specific airway sections and mucus, thus amplifying the effect by impedance matching principle. For example, an intrapulmonary percussive ventilation ("IPV") system working alone tends to push and spread mucus on the airway walls while opening a hole in the middle of the mucus. Adding acoustics to the air pulsations results in the disintegration of the mucus and the movement of particles towards the patient mouthpiece until the airway is nearly completely cleared. For optimization, an algorithm may match the required frequencies, amplitudes, duty cycle, and relative phases of the oscillating air flow and acoustic pulses to the specific patient's geometry and specific secretions.

According to an illustrative embodiment of the present disclosure, a device for unblocking and removing secretions from an airway includes an air flow system and an acoustic system operably coupled to the air flow system. The air flow system includes an air supply, an electrically operable flow control valve in fluid communication with the air supply, and a flow controller in electrical communication with the flow control valve. The acoustic system includes an acoustic pulse generator and an acoustic controller in electrical communication with the acoustic pulse generator. An air flow pathway is in fluid communication with the air flow system and in acoustic communication with the acoustic system. The flow controller causes the flow control valve and the air supply to provide oscillated air flow to the air flow pathway, and the acoustic controller causes the acoustic pulse generator to provide acoustic vibrations to the oscillated air flow.

According to a further illustrative embodiment, the flow controller includes a processor and a memory, the memory including software executed by the processor for defining air flow at a defined air flow frequency and amplitude. In an illustrative embodiment, the defined air flow frequency is between 195 beats per minute ("bpm") and 405 bpm and the defined air flow amplitude is between 15 centimeters of water ("cmH2O") and 55 cmH2O.

According to a further illustrative embodiment, the acoustic controller includes a processor and a memory including software executed by the processor for defining acoustic vibrations at a defined acoustic vibration frequency and amplitude. In an illustrative embodiment, the defined acoustic vibration is between 295 Hertz ("Hz") and 500 Hz.

In an illustrative embodiment, a pressure sensor is operably coupled to the air flow pathway and in communication with the main controller, the main controller being configured to control the air flow system and the acoustic system in response to air pressure detected by the pressure sensor.

According to another illustrative embodiment of the present disclosure, a device for unblocking and removing secretions from an airway includes an air flow pathway, an air flow system in communication with the air flow pathway, and an acoustic system in communication with the air flow pathway. The air flow system includes an air supply, and an electrically operable flow control valve in fluid communication with the air supply. The acoustic system includes a pulse generator configured to generate vibrations. A controller is operably coupled to the air flow system and the acoustic system, the controller being configured to control at least one of frequency, waveform, pressure amplitude, and oscillation duration of air provided by the flow control valve, and the controller configured to control at least one of frequency, amplitude, duty cycle, and relative phase of the vibrations generated by the pulse generator.

According an illustrative embodiment, the controller includes a processor and a memory operably coupled to the processor, wherein software stored within the memory is executed by the processor for defining air flow at a defined air flow frequency and amplitude, and for defining acoustic vibrations at a defined acoustic vibration frequency and amplitude. Illustratively, the defined air flow frequency is between 195 beats per minute and 405 beats per minute, the defined air flow amplitude is between 15 cmH2O and 45 cmH2O, the defined acoustic vibration frequency is between 295 Hertz and 500 Hertz, and the defined acoustic vibration amplitude is between 47 decibels and 109 decibels.

According to a further illustrative embodiment of the present disclosure, a method of unblocking and removing secretions from an airway includes the steps of applying oscillated air flow to an air flow pathway including a secretion and applying acoustic vibrations to the air flow within the air flow pathway. Illustratively, the oscillated air flow is controlled by preprogrammed executable instructions that define at least one of frequency, waveform, pressure amplitude, and oscillation duration. Further illustratively, the acoustic vibrations are controlled by preprogrammed executable instructions that define at least one of frequency, amplitude, duty cycle, and relative phases. In an illustrative embodiment, the method further includes the steps of measuring air pressure within the air flow pathway and adjusting the oscillated air flow and acoustic vibrations in response to the measured air pressure.

According to an illustrative embodiment of the present disclosure, a device for unblocking and removing secretions from airways provides therapy by applying oscillated air flow and acoustic vibrations according to a preprogrammed protocol that defines frequency, waveform, pressure amplitude, and/or oscillation duration through software control.

According to another illustrative embodiment of the present disclosure, a device for unblocking and removing secretions from airways provides therapy by applying oscillated air flow and acoustic vibrations according to an algorithm, stored in a memory as machine readable instructions executed by a processor, that automatically matches the required frequencies, amplitudes, duty cycle, and/or relative phases to a specific patient parameters (e.g., height, weight, geometry, etc.) and/or specific secretion characteristics (e.g., volume, depth, rheological properties (e.g., viscosity and/or elasticity) and/or surface properties (e.g., surface tension, cohesivity and/or adhesivity).

Additional features and advantages of the present invention will become apparent to those skilled in the art upon consideration of the following detailed description of the illustrative embodiment exemplifying the best mode of carrying out the invention as presently perceived.

BRIEF DESCRIPTION OF THE DRAWINGS

The detailed description of the drawings particularly refers to the accompanying figures in which:

FIG. 3 is a diagrammatic view of an illustrative communication system including the illustrative device of FIG. 1 and providing for the transmission of information, such as customized prescription and/or effective treatment procedures, between the patient and a physician;

FIG. 15A is a key diagram, showing utilized solenoid frequencies (Hz) and speaker frequencies (bpm) utilized in the illustrative test setup of FIGS. 4, 5A and 5B to obtain the results illustrated by FIGS. 15B and 15C;

FIG. 15B is a graph illustrating the results obtained for the time to penetration of a simulated secretion blockage or plug within a full-length simulated airway in the illustrative test setup of FIGS. 4, 5A and 5B over a variety of speaker power fractions, solenoid frequencies, and speaker frequencies, wherein the air pressure is set at 40 cmH2O;

FIG. 15C is a graph illustrating the results obtained for the time to penetration of a simulated secretion blockage or plug within a full-length simulated airway in the illustrative test setup of FIGS. 4, 5A and 5B over a variety of speaker power fractions, solenoid frequencies, and speaker frequencies, wherein the air pressure is set at 50 cmH2O;

DETAILED DESCRIPTION OF THE DRAWINGS

The embodiments of the disclosure described herein are not intended to be exhaustive or to limit the disclosure to the precise forms disclosed. Rather, the embodiments described herein enable one skilled in the art to practice the disclosure.

Figure 1:
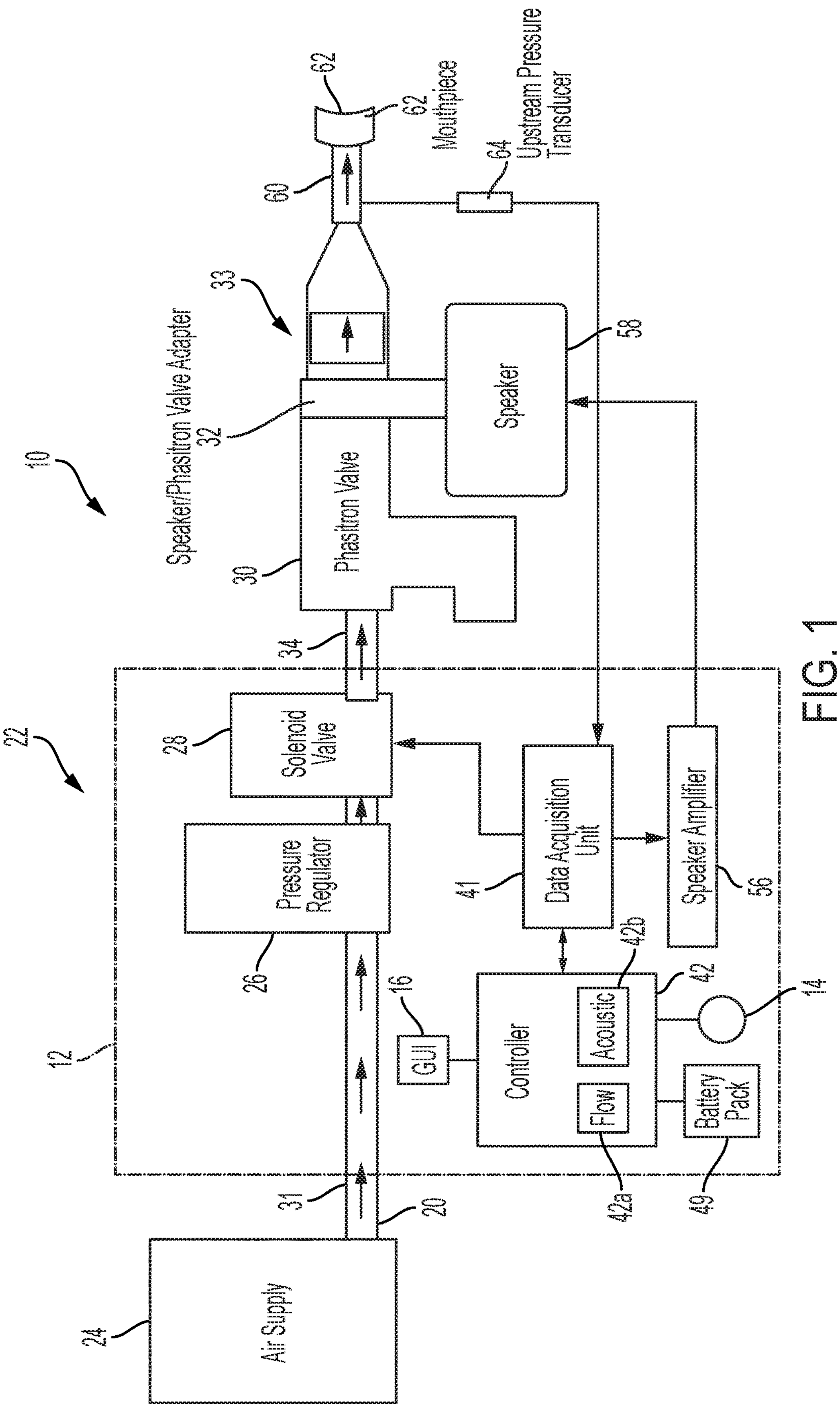
FIG. 1 is a diagrammatic view of an illustrative device of the present disclosure for unblocking and removing secretions from airways, including a cross-sectional view of a device body and showing airflow through the device to a patient mouthpiece.

Referring initially to FIG. 1, an illustrative device for unblocking and removing secretions from airways 10 is shown. The illustrative device 10 may be used for the treatment of a variety of respiratory diseases, e.g. chronic obstructive pulmonary disease, acute bronchiolitis, cystic fibrosis, and other diseases. The illustrative device 10 includes a device body 12 that also serves as the handle for the device 10, allowing the patient to hold the device 10 in one hand during use. The device body 12 of FIG. 1 is shown in cross-section to illustrate contents of the device body 12.

In one illustrative embodiment, a user puts the device 10 into an operational mode via a user input, for example, by pressing a button 14 on the exterior of the device body 12. In another illustrative embodiment, the user operates the device 10 using a graphical user interface ("GUI") 16 supported on a surface of the device body 12. The user may identify that the device 10 is operational by an audible means or through a visual means, for example, text or backlighting on the GUI 16, an operational light on the device body 12, etc.

With further reference to FIG. 1, an air inlet 20 is fluidly coupled to an air flow system 22 to provide air flow to the device 10. The air flow system 22 illustratively includes an air supply 24, a pressure regulator 26 and a control valve 28. The control valve 28 is illustratively an electrically operable valve, such as a solenoid valve. A flow controller, illustratively a ventilator valve 30, is illustratively coupled to the air supply 24. As further detailed herein, the ventilator valve 30 may be defined by an intrapulmonary percussive ventilator ("IPV"). The air inlet 20 may be detachably coupled to a distal end of the device body 12 by an air inlet connector 31, allowing air flow to enter an internal air duct or passageway 34.

Figure 2:
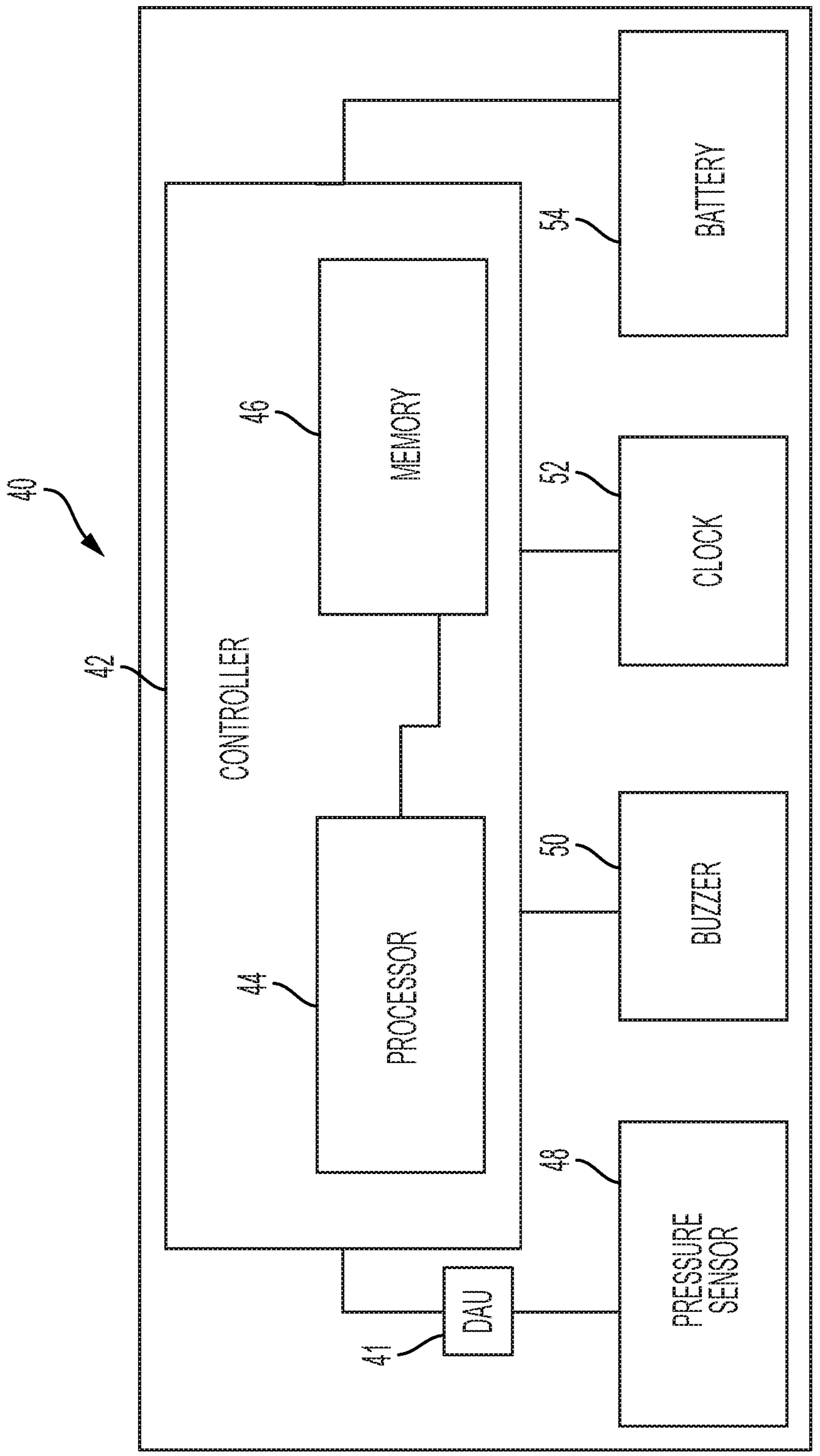
FIG. 2 is a block diagram of an illustrative printed circuit board including the controller of the device of FIG. 1.

As shown in FIG. 2, a printed circuit board 40 is illustratively provided within device body 12 and, in an illustrative embodiment, supports a main controller 42 defined by a processor 44 and a memory 46. The main controller 42 illustratively includes a flow controller **42*a* and an acoustic controller 42*b*. A pressure sensor 48, an audible output device 50 (e.g., a buzzer), a real-time clock 52, and a backup battery 54 for the real-time clock 52 may also be supported by the printed circuit board 40 and are in electrical communication with the main controller 42. Additionally, a data acquisition unit 41 illustratively communicates feedback from the pressure sensor 48 to the main controller 42 during use of the device 10**.

The device 10 is illustratively powered by a rechargeable battery pack 49. Upon battery depletion, the user can charge the battery pack 49 by connecting it to an external, off-the-shelf battery charger. The battery pack 49 illustratively includes a protective circuit to protect the battery pack 49 from over charge, over discharge, maximum cell voltage, and minimum cell voltage.

Referring again to FIGS. 1 and 2, the air inlet 20 is fluidly coupled to the air supply 24 to provide air to body 12 of device 10. In the illustrative embodiment, air supply 24, such as an air blower, may produce air with a pressure of at least 100 pounds per square inch. Illustratively, the air inlet 20 is detachably coupled to a distal end of the device body 12 by the air inlet connector 31, allowing air flow to enter the internal air duct 34. In an illustrative embodiment, the connection between the air inlet 20 and the air inlet connector 31 is configured to provide for a minimum amount of lost air pressure.

As air moves through the device body 12, the processor 44 illustratively operates an air pressure regulator 26 and a solenoid control valve 28 according to a preprogrammed protocol or algorithm stored as machine readable instructions (e.g., software) in the memory 46 of the controller 42. First, the air pressure regulator 26 illustratively adjusts the pressure of the air flow from the air supply 24 to an operable level provided by the preprogrammed protocol or algorithm executed by the controller 42, for example, between 25 and 30 pounds per square inch. The air moves then from the air pressure regulator 26 to the solenoid control valve 28, which illustratively opens and closes at a given frequency provided by the preprogrammed protocol or algorithm executed by the controller 42, for example, between 100 and 300 cycles per minute.

Air then moves from the device body 12 via internal air duct 34 into the ventilator valve 30. The ventilator valve 30 may illustratively be an IPV, such as a Phasitron IPV manufactured by Percussionaire of Sandpoint, Idaho, or a Metaneb IPV manufactured by Hill-Rom, Inc., of Batesville, Indiana. In another illustrative embodiment, the ventilator valve 30 may be comprised of a venturi valve coupled with a T-adapter that may function as an inhalation and exhalation valve. Illustratively, the solenoid valve 28 and/or the pressure regulator 26 may be incorporated within the ventilator valve 30.

In the illustrative embodiment, the air flow system 22 is operably coupled to an acoustic system 33. More particularly, the ventilator valve 30 of the air flow system 22 is operably coupled to an acoustic device or speaker 58 of the acoustic system 33, via a speaker/valve adapter 32. The speaker 58 provides acoustic enhancement to the air within the ventilator valve 30. More particularly, a speaker amplifier 56 may be disposed in the device body 12 and operably coupled to the controller 42 (either directly or via the data acquisition unit 41). The speaker 58 and amplifier 56 may comprise a compression driver unit SD-210R 100 W (neodymium driver) available from Sanming Sound of Huntington Beach, California, or another acoustic device (e.g., speaker and amplifier) capable of delivering up to at least 133 decibels ("dB") of acoustic amplitude between at least 180 Hertz ("Hz") and 7000 Hz in frequency. Illustratively, the controller 42 causes the speaker amplifier 56 to generate acoustic vibration frequencies according to the preprogrammed protocol or algorithm stored in memory 46. Acoustic vibration frequencies may be set at about 100 Hz, about 200 Hz, about 300 Hz, about 400 Hz, about 500 Hz, or about 600 Hz. A maximum acoustic frequency effect has been shown to occur, for example, at about 400 Hz. The speaker amplifier 56 communicates the acoustic vibration frequencies to a speaker 58, adding the vibration frequencies to the oscillated air pressure at the adapter 32.

Still referring to FIG. 1, an air tube or air flow pathway 60 illustratively provides for air flow from the ventilator valve 30 to a patient interface 62, such as a detachable mask or mouthpiece. The detachable mask is configured to be placed over the nose and mouth of the patient during use. Another embodiment may utilize a detachable mouthpiece 62 configured to be used only orally. Free air flow is allowed from air duct 34 through the mouthpiece 62 along an internal air passageway. A patient using mouthpiece 62 can breathe normally while being provided the oscillated air pressure frequencies generated by the solenoid valve 28 and acoustic frequencies provided by the speaker 58. In an illustrative embodiment, a nebulizer may also be included with device 10 to deliver drugs via the respiratory system of the patient as the patient breathes using the device 10.

When the patient exhales into the patient interface 62, he or she may do so freely. During expiration, the device 10 creates expiratory pressure due to the air pressure pulses controlled by the solenoid valve 28. In one illustrative embodiment, the patient may release air from a mouthpiece outlet valve coupled to the pressure sensor 48 supported by the printed circuit board 40. The pressure sensor 48 may comprise an upstream pressure transducer 64 operably coupled to the air flow pathway 60 for measuring the pressure of the outlet air flow. The pressure transducer 64 may comprise a pressure transducer available from Kulite of Leonia, New Jersey.

In another illustrative embodiment, an active controller within the mouthpiece 62 comprises at least one pressure sensor and at least one flow rate sensor and measures airway resistance, thereby providing feedback to the controller 42. More particularly, the measured pressure and flow rate allows the preprogrammed protocol or algorithm within the memory 46 as executed by the processor 44 to optimize the parameters of the device 10 and individualize parameters for each patient based, for example, on the age and size of the patient and the properties of the disease or secretion, i.e. mucus.

In another illustrative embodiment, the processor 44 of the device 10 applies a protocol or algorithm within the memory 46 to personalize and adjust the device's air oscillation and acoustic pulsation according to a response recorded by the memory 46 of the controller 42 during use. The algorithm may also use specific patient parameters (e.g., height, weight, geometry of airway, etc.) and specific secretion characteristics to match the required frequencies, amplitudes, duty cycle, and relative phases of the device 10 to optimize effectiveness for secretion removal. Secretion characteristics may include volume, depth, rheological properties (e.g., viscosity and/or elasticity) and surface properties (e.g., surface tension, cohesivity and/or adhesivity).

FIG. 3 shows an illustrative communication system including the device 10. For example, a sensor 202 measures a breathing response from a patient 204 and communicates the response to a handheld device 206 in possession of the patient 204, such as a tablet or smartphone, using a graphical user interface application 207. The handheld device 206 may also communicate the response to a cloud-base system 208, allowing a physician 201 to access the recorded response and communicate effective treatment 212 with the patient 204.

Figure 4:
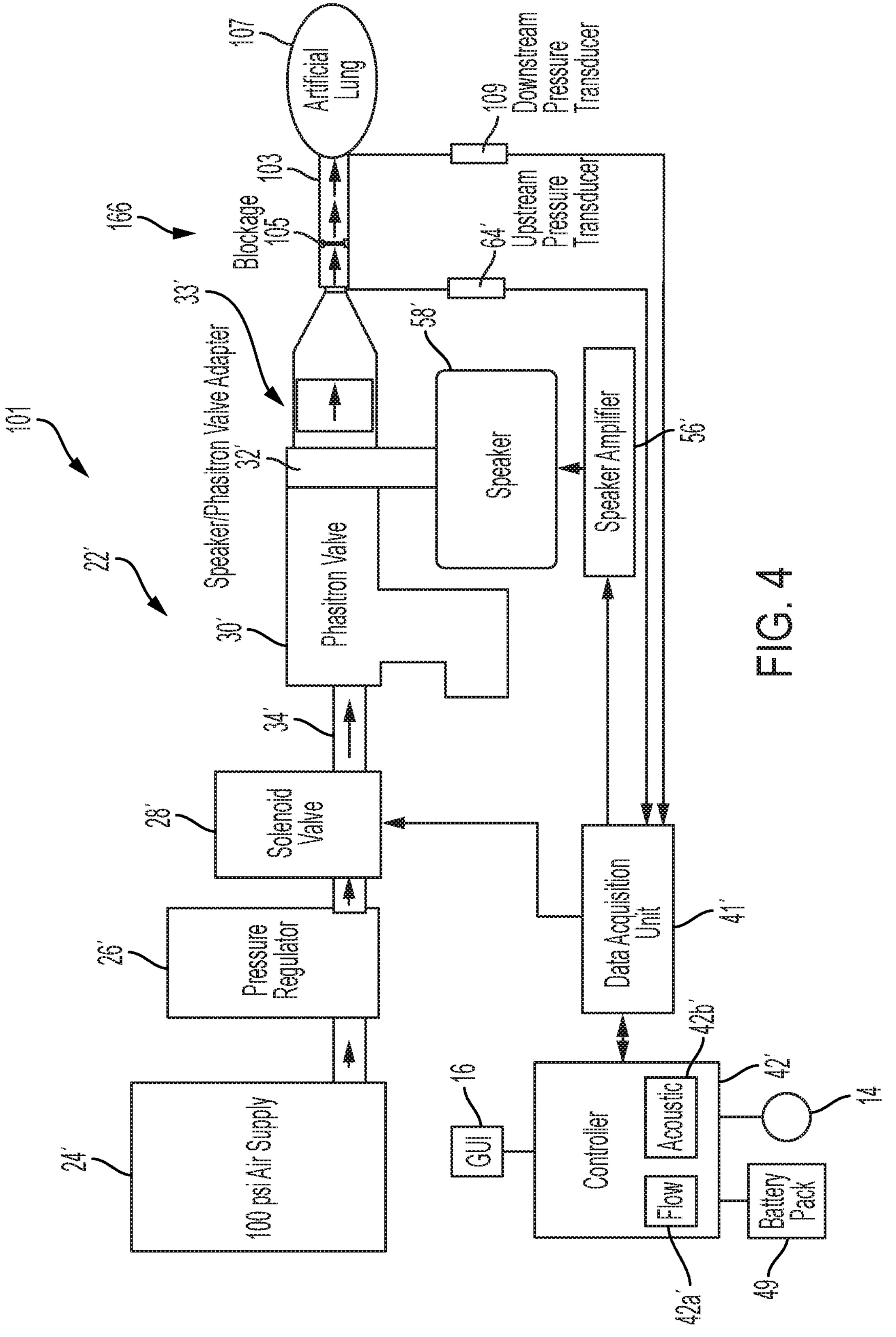
FIG. 4 is a diagrammatic view of an illustrative test setup for the experimental testing of the illustrative device of FIG. 1, showing airflow through the test setup to an artificial lung.
Figure 5A:
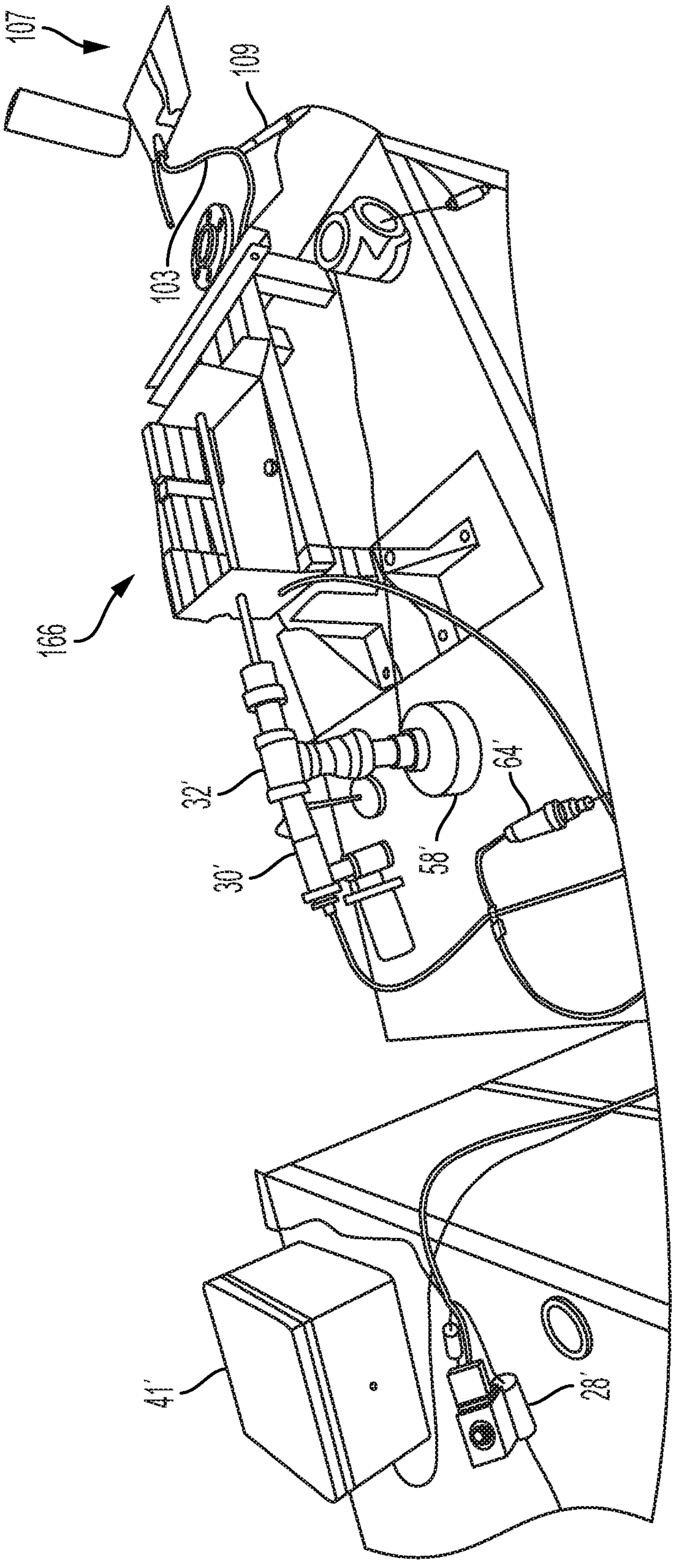
FIG. 5A is a first perspective view of the illustrative test setup of FIG. 4, illustrating the components of the test setup, e.g. a relay box, a solenoid valve, an upstream pressure transducer, a downstream pressure transducer, a ventilator valve, a speaker, a test section, and an artificial lung.
Figure 5B:
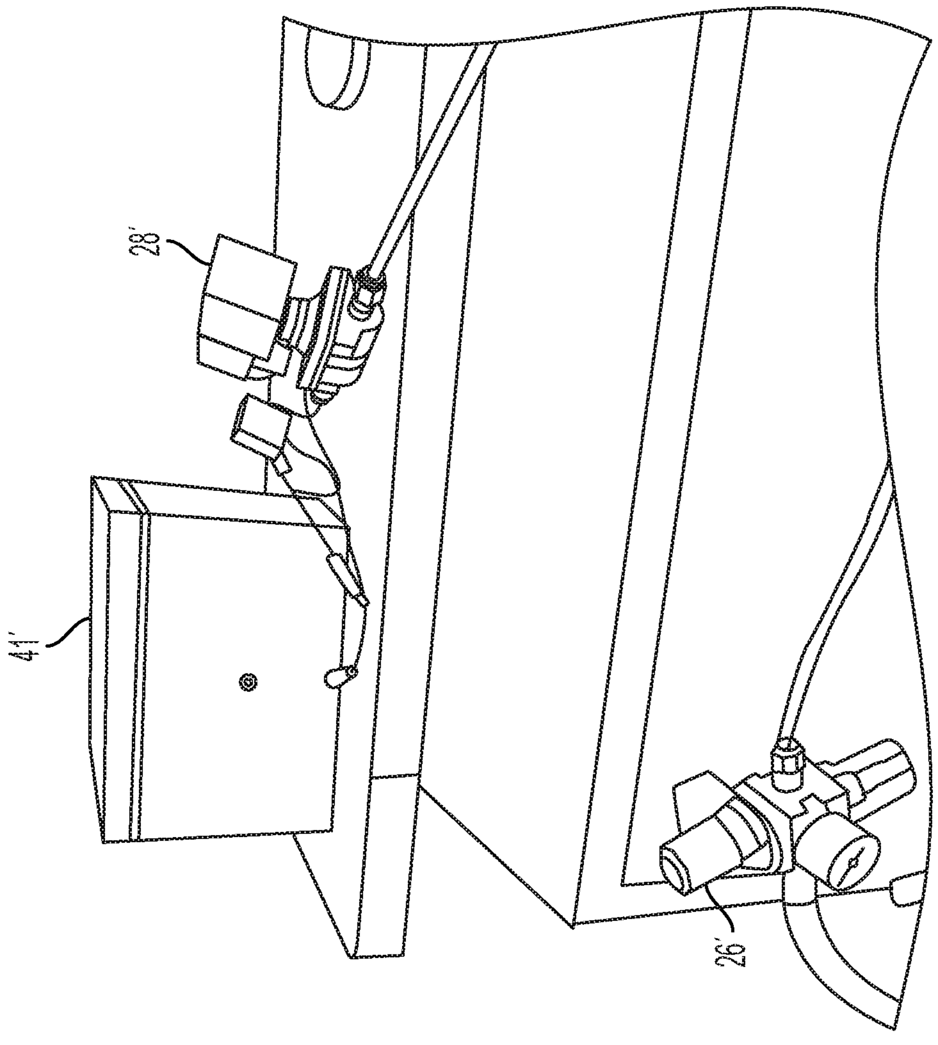
FIG. 5B is a second perspective view of the illustrative test setup of FIG. 4, illustrating a pressure regulator of the test set up relative to the components of the test setup illustrated in FIG. 5A.

FIGS. 4 and 5A-5B illustrate a test setup 101 which may be utilized to test the efficiency and effectiveness of the device 10. Test setup 101 includes many of the same components as device 10, although the components are not necessarily enclosed within a device body 12. As such, similar components include like reference numbers. Additionally, the test setup 101 includes a simulated airway 103, a simulated secretion blockage 105 within the simulated airway 103, and a simulated or artificial lung 107 (e.g., a flexible balloon). A downstream pressure sensor or transducer 109 is located between the simulated airway 103 and the artificial lung 107 and is used to measure the effectiveness of device 10 by measuring the air pressure downstream of the simulated secretion blockage 105 at different device settings. Similar to the upstream pressure transducer 64, the downstream pressure transducer 109 may comprise a pressure transducer available from Kulite of Leonia, New Jersey.

Figure 6:
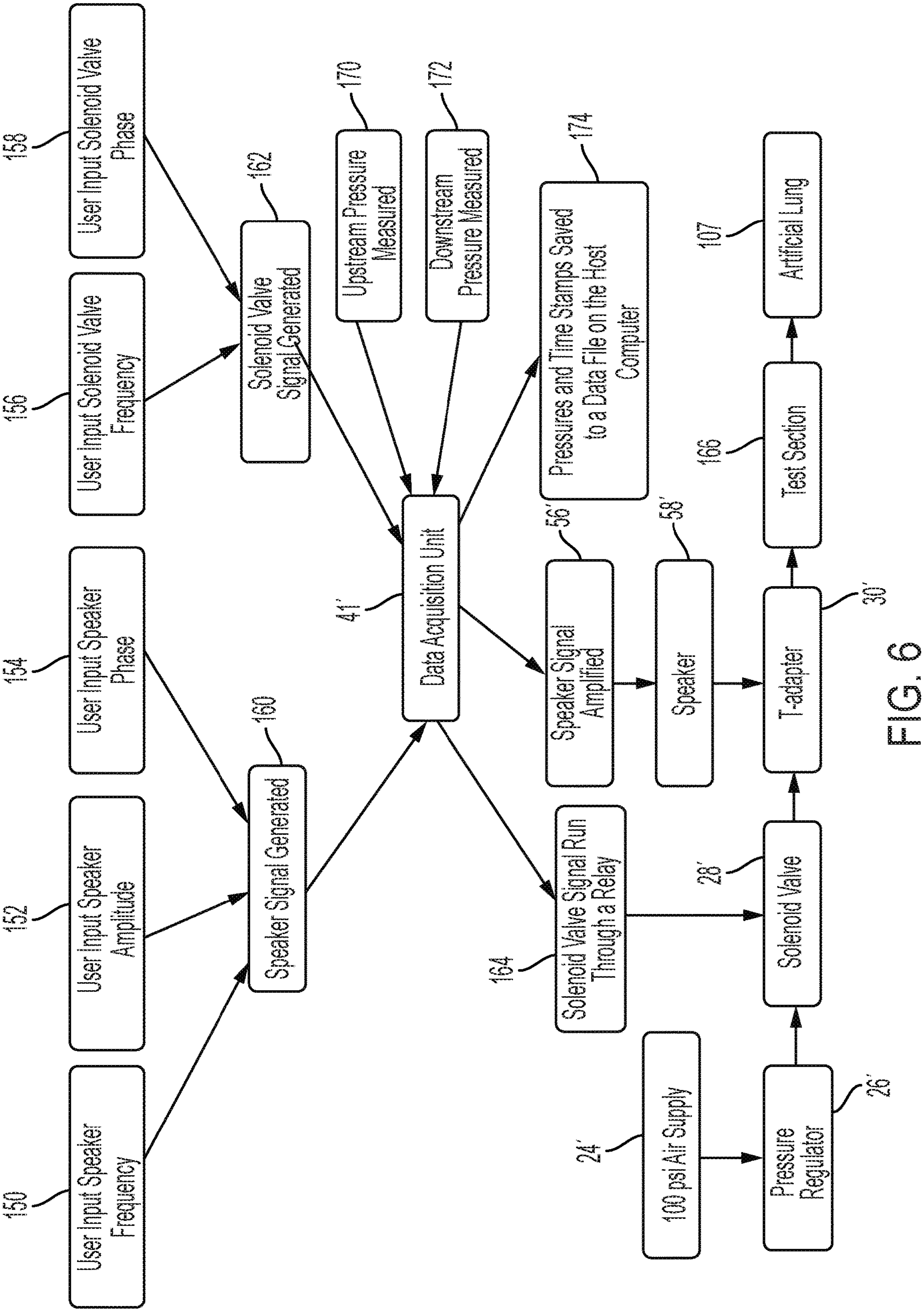
FIG. 6 is a diagrammatic flow chart illustrating the action steps and corresponding structure of the test setup of FIGS. 4, 5A and 5B in an experimental environment.

Referring now to FIGS. 5A-6, a test sequence is illustrated demonstrating the function of the test setup 101 of FIG. 4. For example, referring specifically to FIG. 6, a user may input a desired or defined speaker frequency at input block 150, a desired or defined speaker amplitude at input block 152, and a desired or defined speaker phase at input block 154 into memory 46 of controller 42' via the GUI 16. Software in memory 46 illustratively generates a speaker signal at function block 160 which is then communicated to the data acquisition unit 41'. The user may also input a desired or defined solenoid valve frequency at input block 156 and a desired or defined solenoid valve phase at input block 158 into the software to generate a solenoid valve signal at function block 162 which is also communicated to the data acquisition unit 41'. Varying the speaker phase at input block 154 and the solenoid valve phase at input block 158 allows the user to offset the effects of the speaker 58' and the solenoid valve 28' respectively. The data acquisition unit 41' communicates the solenoid valve signal (generated at function block 162) to a relay 41' (FIGS. 5A-5B) as per function box 164 to operate the solenoid valve 28' in accordance with the solenoid valve signal (generated at function block 162). The data acquisition unit 41' also amplifies the speaker signal (generated at function block 160) via a speaker amplifier 56' to operate the speaker 58' in accordance with the speaker signal (generated at function block 160).

Referring further to FIGS. 5A-6, the air supply 24' provides air to the test setup 101; illustratively, the air supply 24' provides air flow at an air pressure of approximately 100 pounds per square inch ("psi") or approximately 7030.7 centimeters of water ("cmH2O"). The air moves through a pressure regulator 26', which regulates the pressure of the air flow to an operable level as described above. The air then flows from the pressure regulator 26' to the solenoid valve 28', operated as described above, and then into the ventilator valve 30', illustratively coupled to a T-adapter. The air is acoustically enhanced via the speaker 58' coupled to the ventilator valve 30', which is operated as described above. The air is then free to enter the test section 166, including the simulated airway 103 containing a blockage 105 comprising simulated secretion with an artificial lung 107 coupled to a distal end of the simulated airway 103 opposite the ventilator valve 30'.

The upstream pressure transducer 64' and the downstream pressure transducer 109 measure the upstream air pressure at function block 170 and the downstream air pressure at function block 172, respectively, and communicate the measured pressure data to the data acquisition unit 41'. The data acquisition unit 41' then transmits the measured pressures and time stamps to a data file in memory 46 of the controller 42 for later analyzation and utilization as per function block 174.

For testing purposes, naturally occurring human secretions (e.g., blockage 105), including mucus, may be modeled by simulated materials. The simulated materials are illustratively selected based upon properties that generate behavior mimicking that of secretion, such as viscosity and surface tension. Various secretion characteristics may include volume, depth, rheological properties (e.g., viscosity and/or elasticity) and surface properties (e.g., surface tension, cohesivity and/or adhesivity).

For example, one simulated material used may be mayonnaise. In other embodiments, the simulated material may be a thixotropic material. For example, a volume of one cup of such thixotropic material may include: 1) one-third cup of 40-60 glycerol-water mixture; 2) one-half cup of lubricating gel, such as Lubri Gel or K-Y Gel; 3) five teaspoons of powder having nanoparticles in the size of 20 to 50 microns, such as water-soluble poly(ethylene) oxide polymers (Polyox), alumina, salts, and talcum powder; and 4) five to 10 cc food coloring or two teaspoons of instant coffee. In additional embodiments, guar gum, tetraborate, or locust bean gum may be used in place of mucus for testing purposes. Galactomannan gum, a substance derived of locust beans and comprising galactose and mannose in a ratio of one galactose unit per four mannose units, and scleroglucan, a substance obtained through aerobic fermentation of the *Sclerotium* fungus, may additionally be used in place of mucus or other secretion for testing purposes.

The viscosity of the simulated material may be altered by varying the size of the powder, while paraffin oil may be used to reduce surface tension. Surface tension, viscosity, and temperature also share a strong dependence. An illustrative contact angle of the simulated material is about 75 degrees, which may be measured by taking a drop of simulated material about two millimeters in diameter and measuring the side elevation. Alternatively, an optical viscosity meter may be used.

Figure 7A:
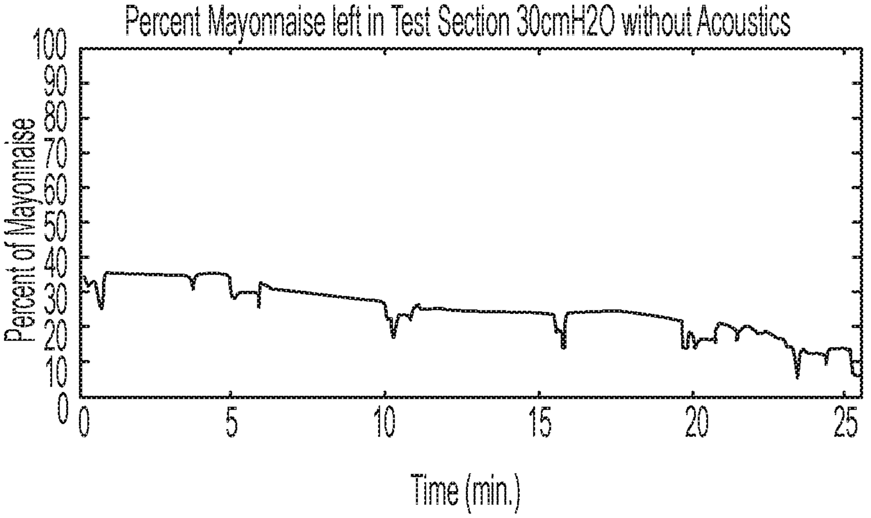
FIG. 7A is a graph illustrating results obtained for removing a blockage or plug of simulated secretion from a simulated airway using air pressure oscillations alone in the illustrative test setup of FIG. 4, wherein the ventilator valve used for testing purposes is a Percussionaire intrapulmonary ventilator and the air pressure is set at 30 cmH2O.
Figure 7B:
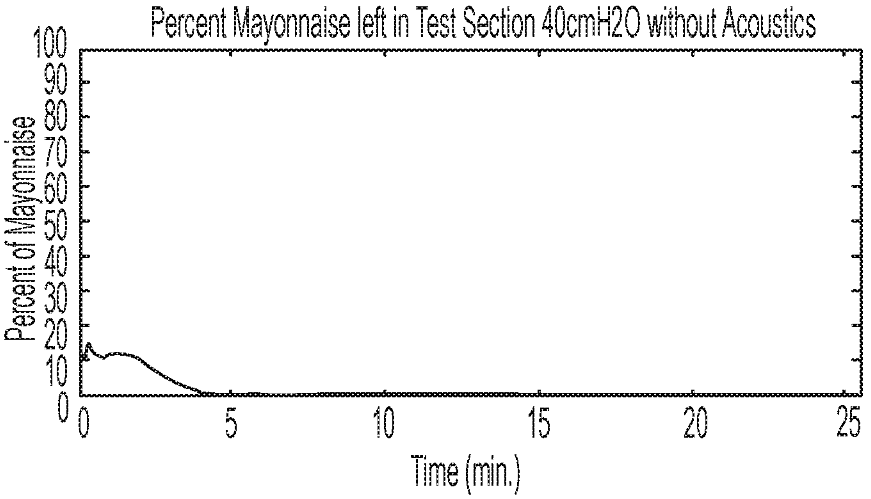
FIG. 7B is a graph illustrating results obtained for removing a blockage or plug of simulated secretion from a simulated airway using air pressure oscillations alone in the illustrative test setup of FIG. 4, wherein the ventilator valve used for testing purposes is a Percussionaire intrapulmonary ventilator and the air pressure is set at 40 cmH2O.
Figure 7C:
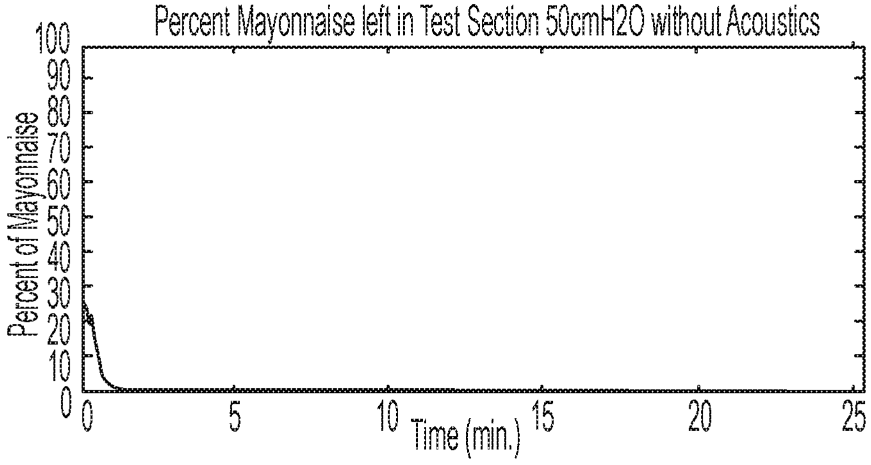
FIG. 7C is a graph illustrating results obtained for removing a blockage or plug of simulated secretion from a simulated airway using air pressure oscillations alone in the illustrative test setup of FIG. 4, wherein the ventilator valve used for testing purposes is a Percussionaire intrapulmonary ventilator and the air pressure is set at 50 cmH2O.
Figure 8A:
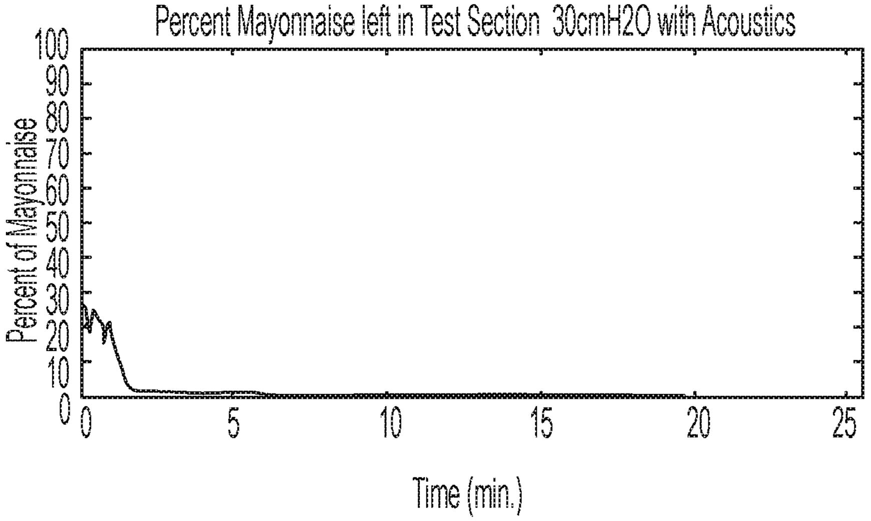
FIG. 8A is a graph illustrating results obtained for removing a blockage or plug of simulated secretion from a simulated airway using both acoustic supplementation and air pressure oscillations combined in the illustrative test setup of FIG. 4, wherein the ventilator valve used for testing purposes is a Percussionaire intrapulmonary ventilator and the air pressure is set at 30 cmH2O.
Figure 8B:
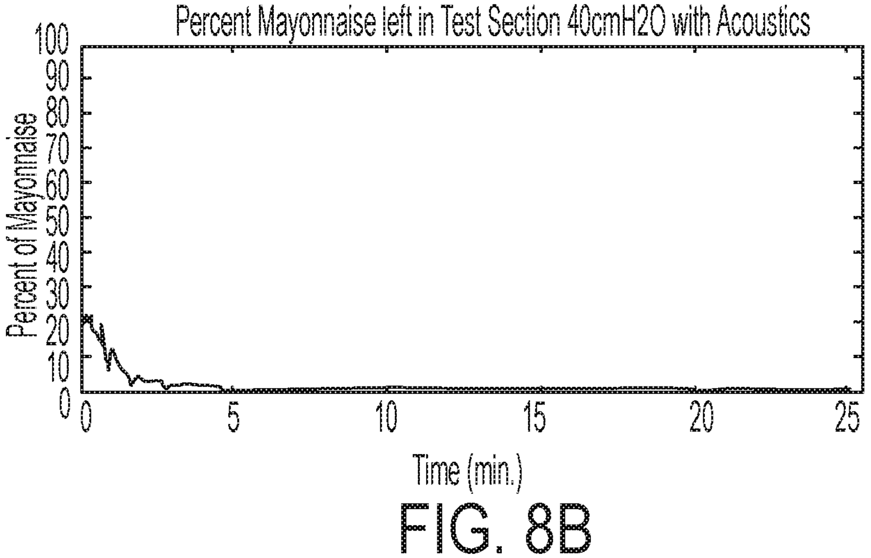
FIG. 8B is a graph illustrating results obtained for removing a blockage or plug of simulated secretion from a simulated airway using both acoustic supplementation and air pressure oscillations combined in the illustrative test setup of FIG. 4, wherein the ventilator valve used for testing purposes is a Percussionaire intrapulmonary ventilator and the air pressure is set at 40 cmH2O.
Figure 8C:
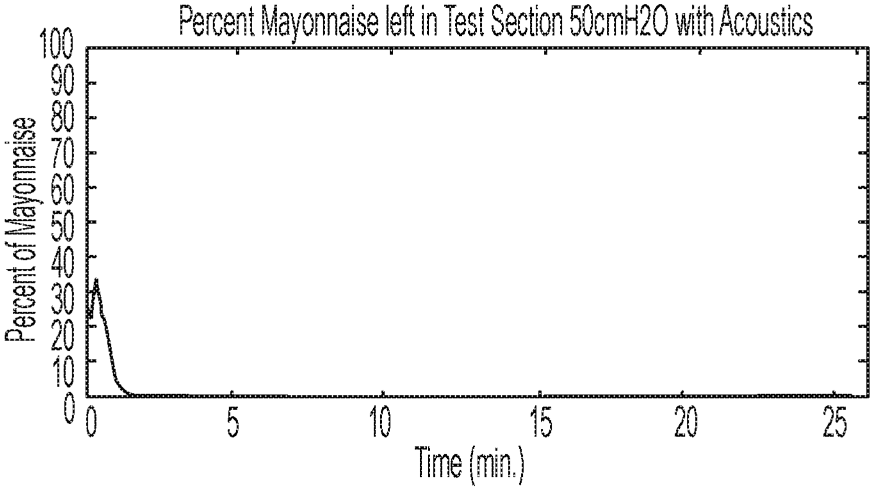
FIG. 8C is a graph illustrating results obtained for removing a blockage or plug of simulated secretion from a simulated airway using both acoustic supplementation and air pressure oscillations combined in the illustrative test setup of FIG. 4, wherein the ventilator valve used for testing purposes is a Percussionaire intrapulmonary ventilator and the air pressure is set at 50 cmH2O.

During illustrative testing, video of the airway simulator may be recorded to post-process and quantify the amount of secretion in the airway simulator as a function of test duration and direction of secretion motion. With reference to FIGS. 7A-10B, preliminary results are presented. The results show that flow rates, flow pulsations, and acoustic frequencies affect the removal of simulated material (blockage) from simulated airways and should not be interpreted as indicating positive or negative trends. Referring specifically to FIGS. 7A-7C and 8A-8C, data from a test setup utilizing a Percussionaire IPV-1C unit is presented. FIGS. 7A, 7B and 7C display the percentage of simulated secretion remaining in the simulated airway when the test was performed without the use of acoustics and using an air pressure of 30 cmH2O, 40 cmH2O, and 50 cmH2O respectively. Meanwhile, FIGS. 8A, 8B and 8C display the percentage of simulated secretion remaining in the simulated airway when the test was performed with the use of acoustics. As can be shown by comparing FIG. 7A with FIG. 8A, FIG. 7B with FIG. 8B, etc., acoustic enhancement of the air flow results in faster removal of the simulated secretion from the simulated airway.

Figure 9B:
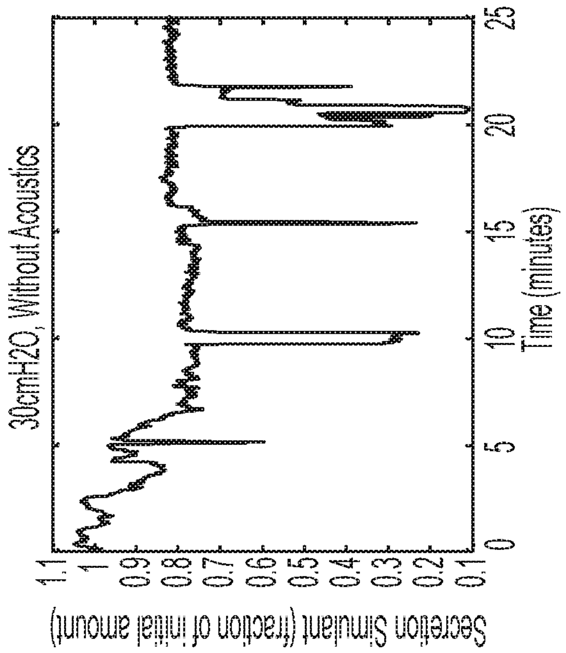
FIG. 9B is another graph illustrating results obtained for removing a blockage or plug of simulated secretion from a simulated airway using air pressure oscillations alone in the illustrative test setup of FIG. 4, wherein the ventilator valve used for testing purposes is a Percussionaire intrapulmonary ventilator and the air pressure is set at 30 cmH2O.
Figure 9A:
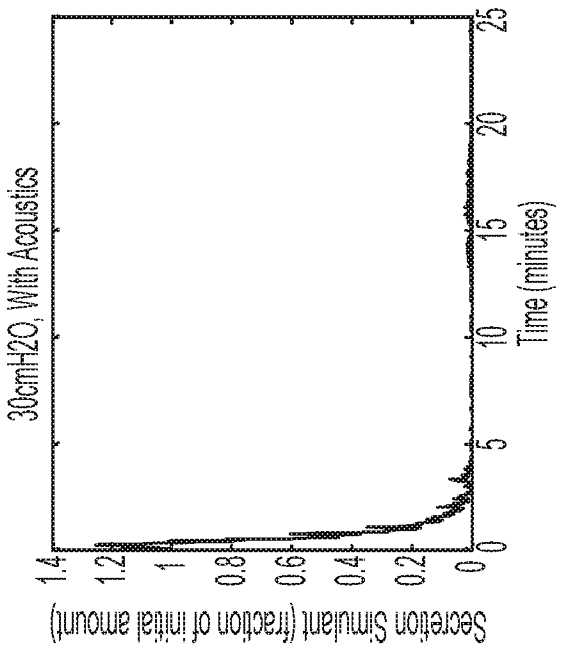
FIG. 9A is another graph illustrating results obtained for removing a blockage or plug of simulated secretion from a simulated airway using both acoustic supplementation and air pressure oscillations combined in the illustrative test setup of FIG. 4, wherein the ventilator valve used for testing purposes is a Percussionaire intrapulmonary ventilator and the air pressure is set at 30 cmH2O.

Additional graphical comparison of the amount of simulated secretion in the simulated airway of a test setup utilizing a Percussionaire IPV system with a set air pressure of 30 cmH2O is shown in FIGS. 9A and 9B. FIG. 9A shows the percentage of simulated secretion remaining in the simulated airway using the acoustically enhanced system over time, while FIG. 9B shows the percentage of simulated secretion left in the simulated airway over time when the standard system (i.e., without acoustics) is used. As shown, the enhanced system can clear the secretion significantly faster than the standard system.

Figure 10B:
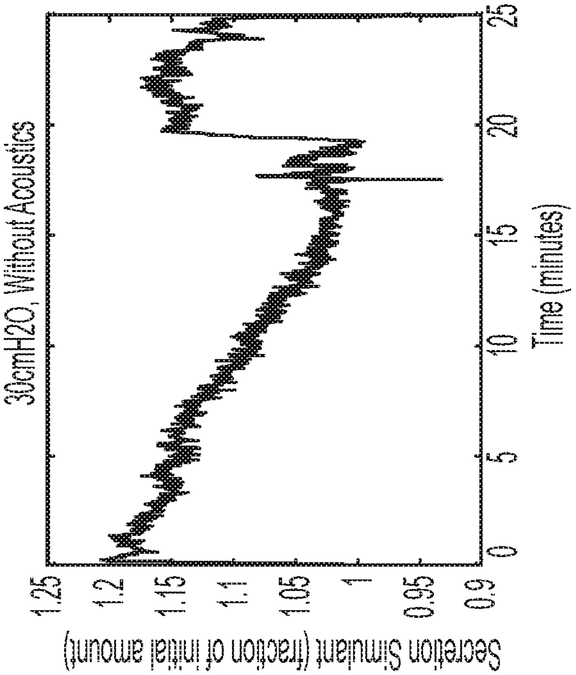
FIG. 10B is a graph illustrating results obtained for removing a blockage or plug of simulated secretion from a simulated airway using air pressure oscillations alone in the illustrative test setup of FIG. 4, wherein the ventilator valve used for testing purposes is a Hill-Rom Metaneb intrapulmonary ventilator and the air pressure is set at 30 cmH2O.
Figure 10A:
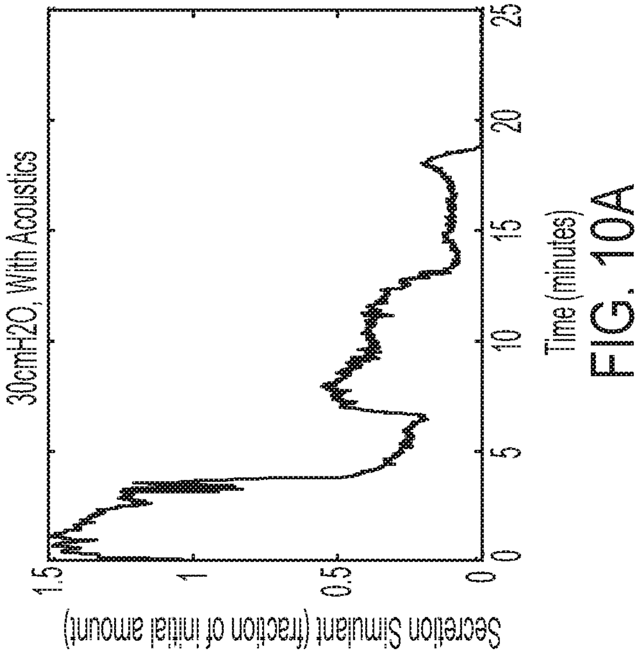
FIG. 10A is a graph illustrating results obtained for removing a blockage or plug of simulated secretion from a simulated airway using both acoustic supplementation and air pressure oscillations combined in the illustrative test setup of FIG. 4, wherein the ventilator valve used for testing purposes is a Hill-Rom Metaneb intrapulmonary ventilator and the air pressure is set at 30 cmH2O.

Alternately, a graphical comparison of the amount of simulated secretion in the simulated airway of a test setup utilizing a Hill-Rom MetaNeb IPV system with a set air pressure of 30 cmH2O is shown in FIGS. 10A and 10B. FIG. 10A shows the percentage of simulated secretion remaining in the simulated airway using the acoustically enhanced system over time, while FIG. 10B shows the percentage of simulated secretion left in the simulated airway over time when the standard system (i.e., without acoustics) is used. As shown, the enhanced system clears the secretion significantly faster than the standard system.

Figure 11:
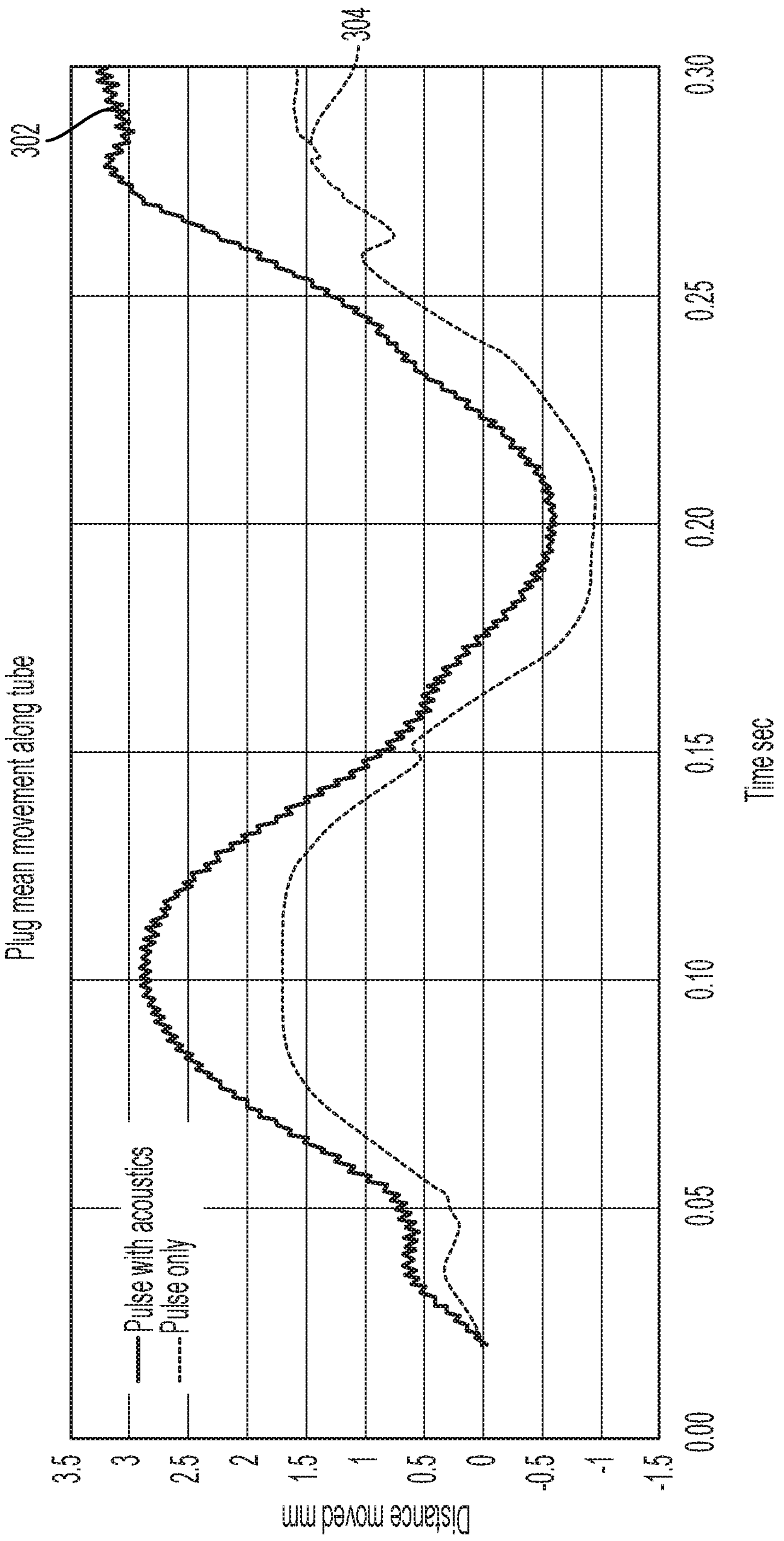
FIG. 11 is a graph comparing results obtained for measuring the movement of a simulated secretion blockage or plug within a simulated airway in the illustrative test setup of FIGS. 4, 5A and 5B, wherein the results of a test setup using air pressure oscillations alone is compared to the results of a test setup using both air pressure oscillations combined with acoustic supplementation.
Figure 12:
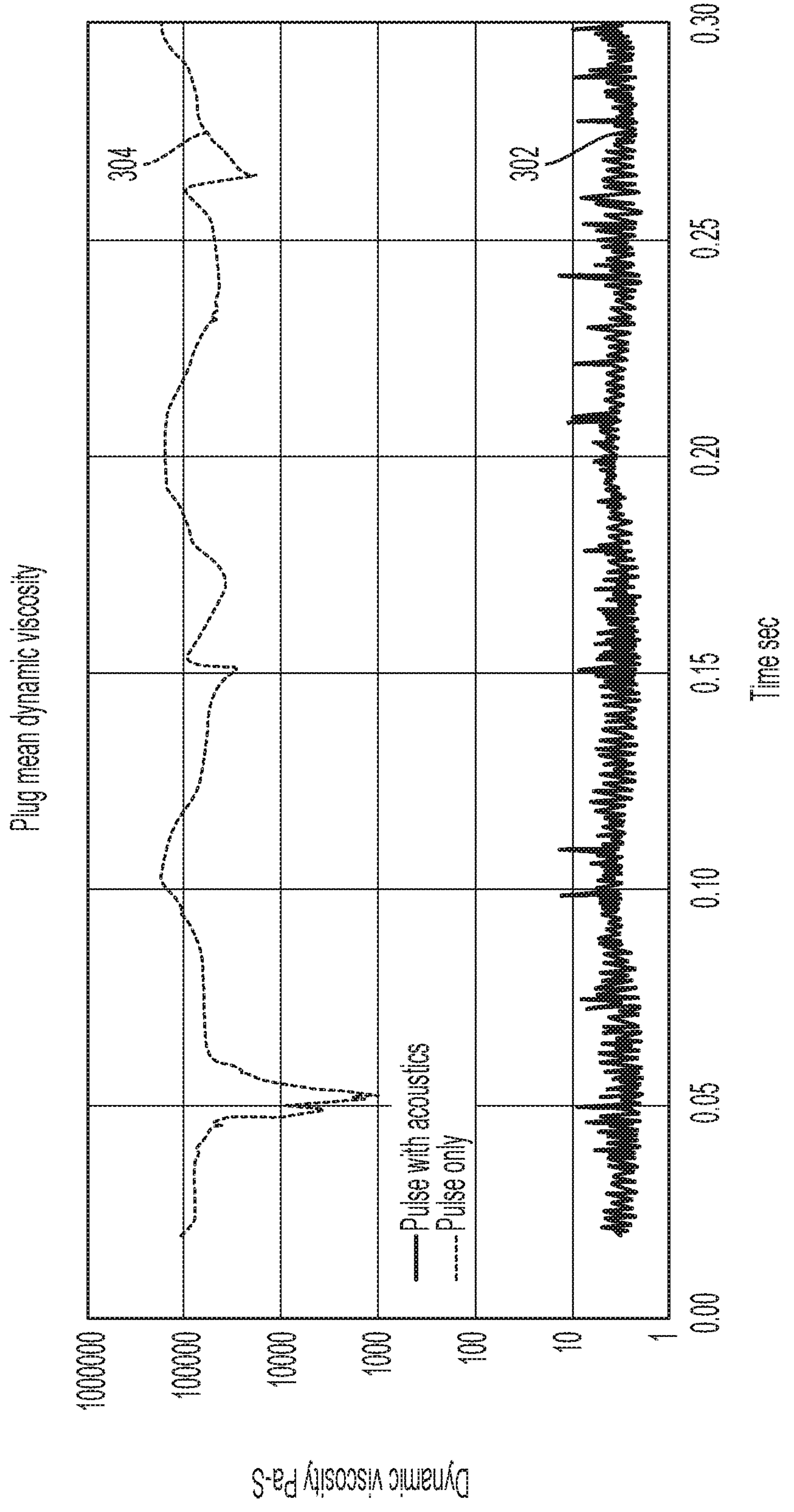
FIG. 12 is a graph comparing results obtained for measuring the mean dynamic viscosity of a simulated secretion blockage or plug within a simulated airway in the illustrative test setup of FIGS. 4, 5A and 5B, wherein the results of a test setup using air pressure oscillations alone is compared to the results of a test setup using both air pressure oscillations combined with acoustic supplementation.
Figure 13:
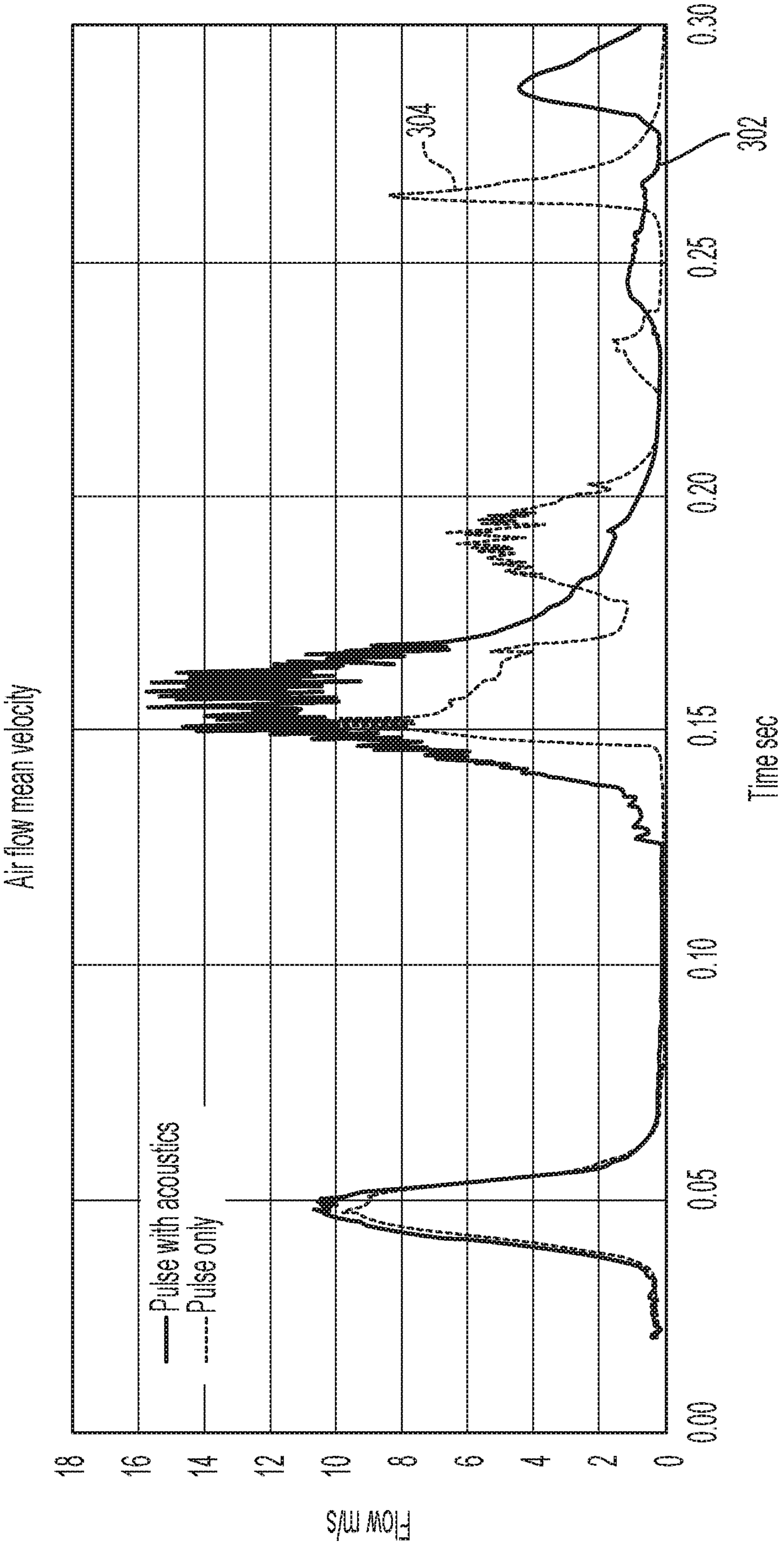
FIG. 13 is a graph comparing results obtained for the air flow mean velocity through the test section of the illustrative test setup of FIGS. 4, 5A and 5B, wherein the results of a test setup using air pressure oscillations alone is compared to the results of a test setup using both air pressure oscillations combined with acoustic supplementation.

Referring now to FIGS. 11-13, additional data is portrayed to demonstrate the different effects of air flow pulsations without acoustic enhancement as compared to air flow pulsations with acoustic enhancement. In each of FIGS. 11-13, line 302 demonstrates the effect of acoustically enhanced air pulsations, while line 304 demonstrates the effect of air pulsations without acoustic enhancement. Specifically, FIG. 11 measures the movement of a simulated secretion blockage within the simulated airway during testing. As shown, the secretion blockage is more effectively moved by air pulsations that have been acoustically enhanced than by air pulsations without acoustic enhancement.

Now referring to FIG. 12, the comparative viscosity of the simulated secretion used during testing is measured in systems using acoustically enhanced air pulsations as compared to systems utilizing air pulsations without acoustic enhancement. As viscosity of secretion becomes lower, it is easier to penetrate using the air pulsations and also more effectively moves within the airway, facilitating the removal of the secretion from the airway. As demonstrated, the viscosity of secretion drops demonstrably in systems utilizing acoustic enhancement versus systems that do not use acoustics.

FIG. 13 demonstrates the average air flow velocity of the air moving into the artificial lung of a test setup. In an airway with a blockage of secretion, less air flow is moving into the lung than would be moving into the lung in an airway without a blockage of secretion. The air flow velocity of air pulsations which have been acoustically enhanced is higher than the air flow velocity of air pulsations without acoustic enhancement. Additionally, acoustic enhancement results in oscillation of the air flow, which has a pronounced effect on the simulated secretion.

Figure 14B:
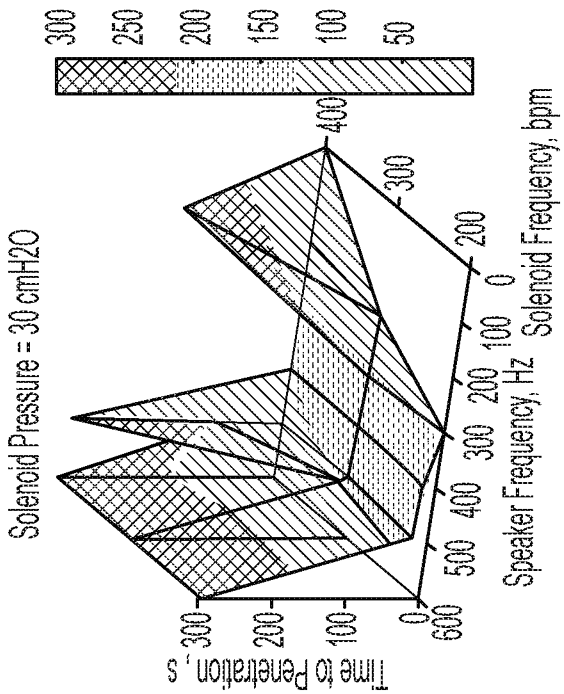
FIG. 14B is a graph illustrating the results obtained for the time to penetration of a simulated secretion blockage or plug within a simulated airway in the illustrative test setup of FIGS. 4, 5A and 5B using a combination of air pressure oscillations over varied frequencies and acoustic supplementation over varied frequencies, wherein the air pressure is set at 30 cmH2O.
Figure 14A:
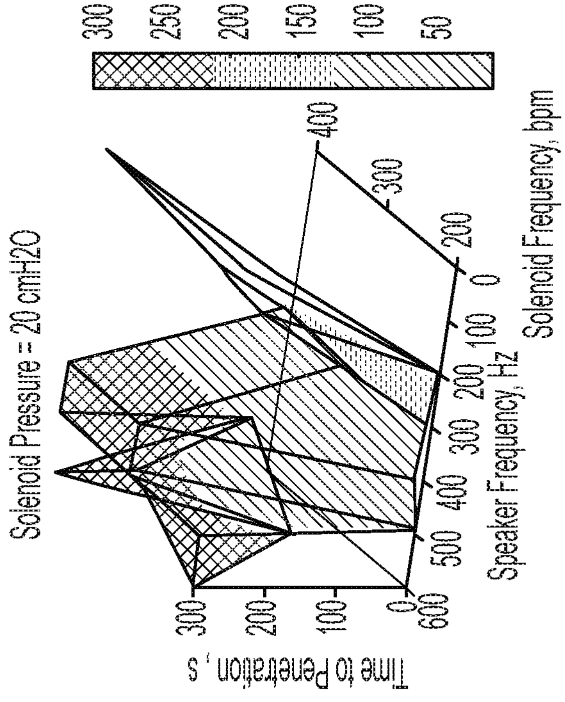
FIG. 14A is a graph illustrating the results obtained for the time to penetration of a simulated secretion blockage or plug within a simulated airway in the illustrative test setup of FIGS. 4, 5A and 5B using a combination of air pressure oscillations over varied frequencies and acoustic supplementation over varied frequencies, wherein the air pressure is set at 20 cmH2O.
Figure 14C:
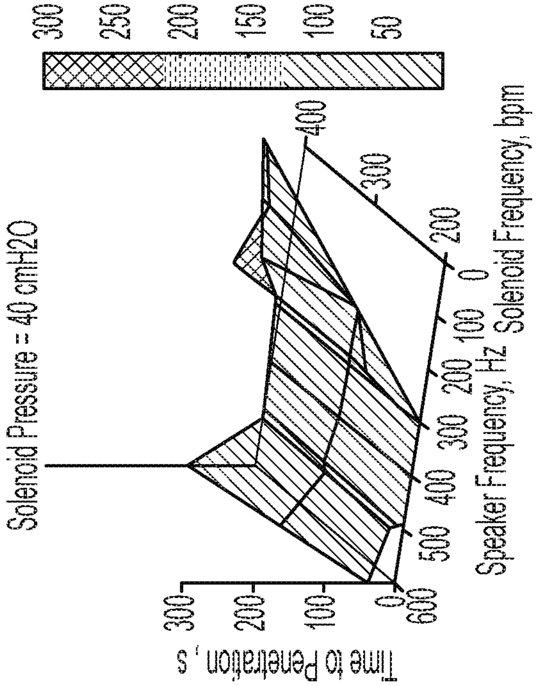
FIG. 14C is a graph illustrating the results obtained for the time to penetration of a simulated secretion blockage or plug within a simulated airway in the illustrative test setup of FIGS. 4, 5A and 5B using a combination of air pressure oscillations over varied frequencies and acoustic supplementation over varied frequencies, wherein the air pressure is set at 40 cmH2O.
Figure 14D:
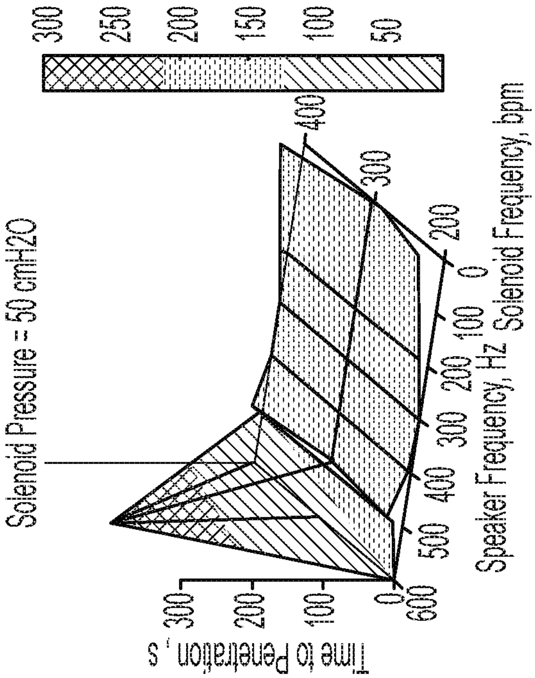
FIG. 14D is a graph illustrating the results obtained for the time to penetration of a simulated secretion blockage or plug within a simulated airway in the illustrative test setup of FIGS. 4, 5A and 5B using a combination of air pressure oscillations over varied frequencies and acoustic supplementation over varied frequencies, wherein the air pressure is set at 50 cmH2O.
Figure 16A:
FIG. 16A is a graph illustrating the results obtained for the time to penetration of a simulated secretion blockage or plug within either a full-length simulated airway or a half-length simulated airway in the illustrative test setup of FIGS. 4, 5A and 5B over a variety of speaker power fractions, wherein the air pressure is set at 40 cmH2O, the solenoid frequency is set at 300 bpm, and the speaker frequency is set at 300 Hz.
Figure 16B:
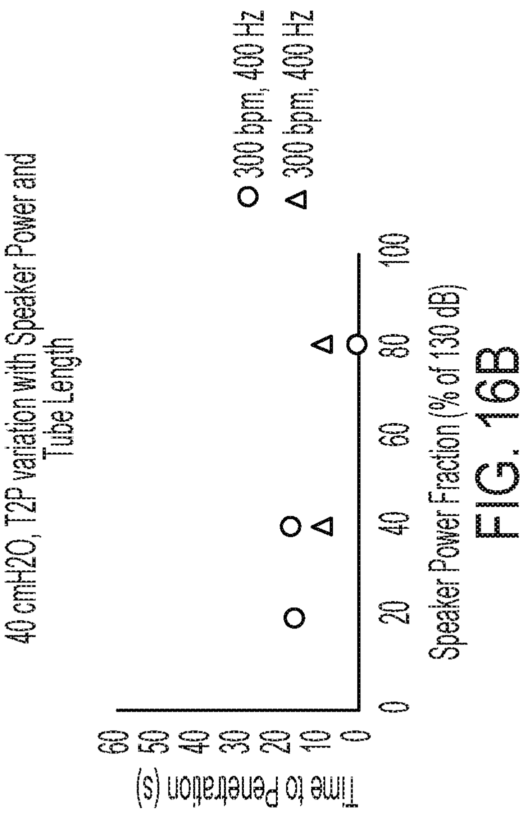
FIG. 16B is a graph illustrating the results obtained for the time to penetration of a simulated secretion blockage within either a full-length simulated airway or a half-length simulated airway in the illustrative test setup of FIGS. 4, 5A and 5B over a variety of speaker power fractions, wherein the air pressure is set at 40 cmH2O, the solenoid frequency is set at 300 bpm, and the speaker frequency is set at 400 Hz.
Figure 16C:
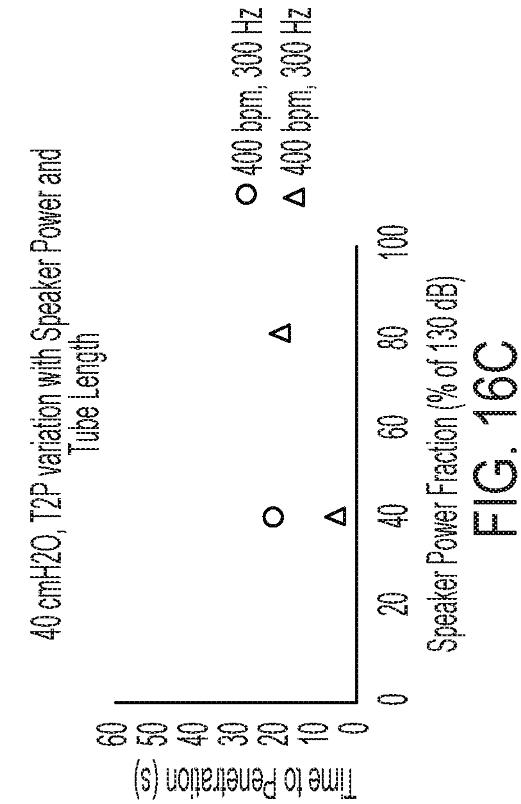
FIG. 16C is a graph illustrating the results obtained for the time to penetration of a simulated secretion blockage or plug within either a full-length simulated airway or a half-length simulated airway in the illustrative test setup of FIGS. 4, 5A and 5B over a variety of speaker power fractions, wherein the air pressure is set at 40 cmH2O, the solenoid frequency is set at 400 bpm, and the speaker frequency is set at 300 Hz.
Figure 16D:
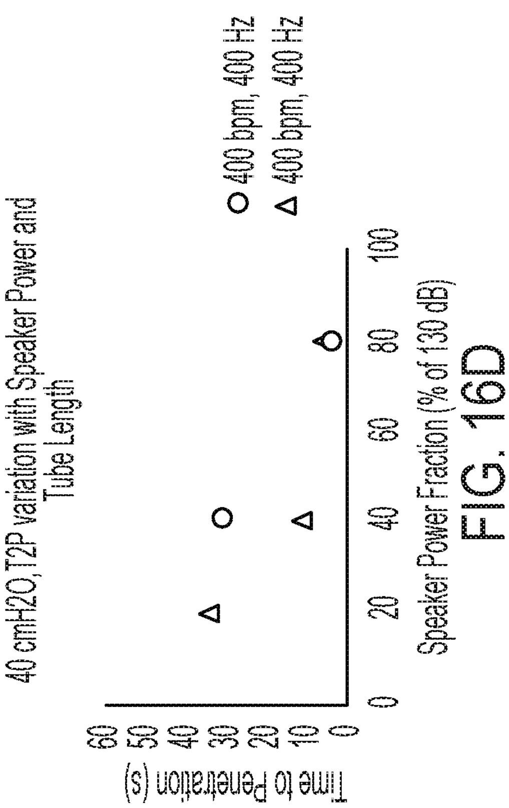
FIG. 16D is a graph illustrating the results obtained for the time to penetration of a simulated secretion blockage or plug within either a full-length simulated airway or a half-length simulated airway in the illustrative test setup of FIGS. 4, 5A and 5B over a variety of speaker power fractions, wherein the air pressure is set at 40 cmH2O, the solenoid frequency is set at 400 bpm, and the speaker frequency is set at 400 Hz.
Figure 17A:
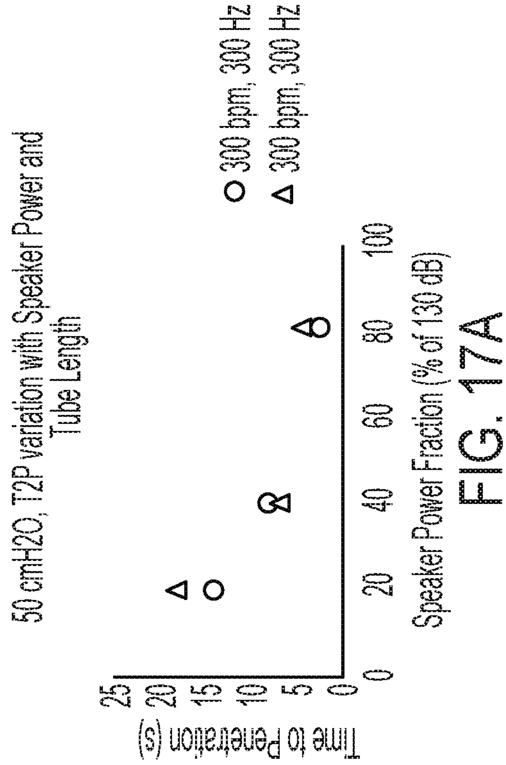
FIG. 17A is a graph illustrating the results obtained for the time to penetration of a simulated secretion blockage or plug within either a full-length simulated airway or a half-length simulated airway in the illustrative test setup of FIGS. 4, 5A and 5B over a variety of speaker power fractions, wherein the air pressure is set at 50 cmH2O, the solenoid frequency is set at 300 bpm, and the speaker frequency is set at 300 Hz.
Figure 17B:
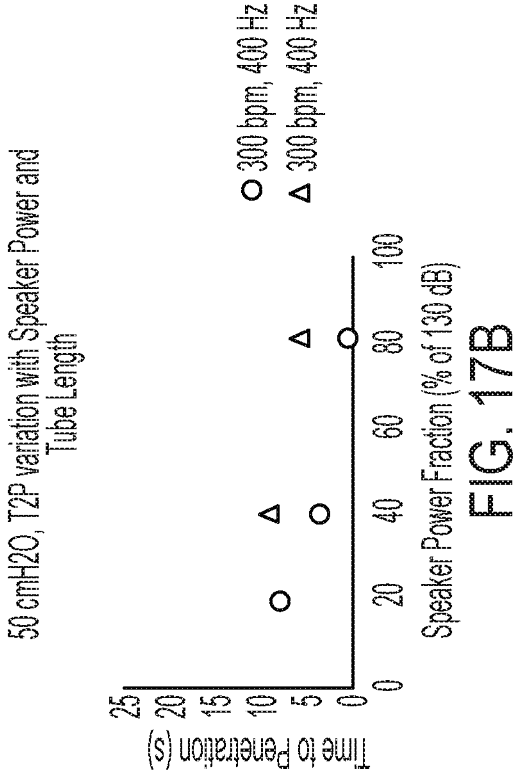
FIG. 17B is a graph illustrating the results obtained for the time to penetration of a simulated secretion blockage or plug within either a full-length simulated airway or a half-length simulated airway in the illustrative test setup of FIGS. 4, 5A and 5B over a variety of speaker power fractions, wherein the air pressure is set at 50 cmH2O, the solenoid frequency is set at 300 bpm, and the speaker frequency is set at 400 Hz.
Figure 17C:
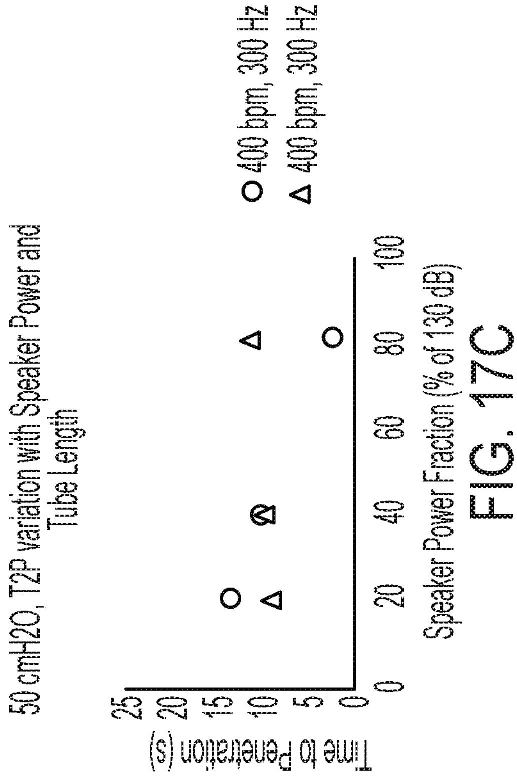
FIG. 17C is a graph illustrating the results obtained for the time to penetration of a simulated secretion blockage or plug within either a full-length simulated airway or a half-length simulated airway in the illustrative test setup of FIGS. 4, 5A and 5B over a variety of speaker power fractions, wherein the air pressure is set at 50 cmH2O, the solenoid frequency is set at 400 bpm, and the speaker frequency is set at 300 Hz.
Figure 17D:
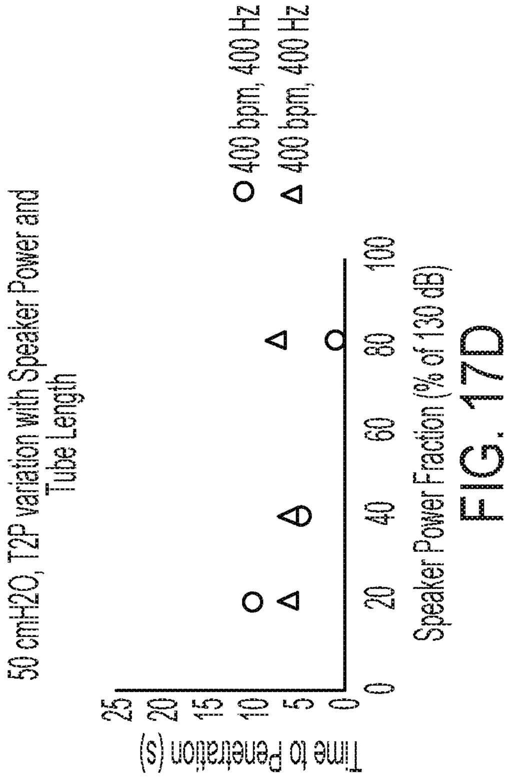
FIG. 17D is a graph illustrating the results obtained for the time to penetration of a simulated secretion blockage or plug within either a full-length simulated airway or a half-length simulated airway in the illustrative test setup of FIGS. 4, 5A and 5B over a variety of speaker power fractions, wherein the air pressure is set at 50 cmH2O, the solenoid frequency is set at 400 bpm, and the speaker frequency is set at 400 Hz.

In the event an airway is completely blocked by secretion, it is desirable to penetrate the blockage caused by secretion to allow the user to breathe and to better facilitate the removal of secretion from the airway using the device 10 (FIG. 1). A graphical representation of the ability of the device 10 (FIG. 1) to penetrate a secretion blockage at a consistent solenoid pressure and speaker power percentage is portrayed by FIGS. 14A-14D. When the time to penetration reaches or surpasses 300 seconds, it is assumed the secretion blockage was not penetrated before it was pushed into the artificial lung being used for testing. For example, FIG. 14A demonstrates that the secretion blockage was not penetrated before being pushed into the artificial lung when the speaker frequency was between 400 Hz and 500 Hz with a constant air pressure at 20 cmH2O. Looking collectively at FIGS. 14A-14D, the middle range frequencies, e.g. 300-490 Hz, penetrate the secretion blockage more quickly than the top range or the bottom range of frequencies tested. Additionally, higher solenoid pressures more consistently penetrate the secretion blockage at a quicker pace than lower supply pressures.

The effect of speaker power reduction on the ability of the device 10 (FIG. 1) to penetrate a secretion blockage is demonstrated by FIGS. 15B-15C using the legend of FIG. 15A. Where points are not plotted on the graph, or replaced with arrows, it is assumed that penetration does not occur before the blockage is pushed into the artificial lung used in testing. Specifically, in FIG. 15B, the points plotted on the graph show the time to penetration at varying solenoid valve frequencies and speaker frequencies with a consistent air pressure of 40 cmH2O over a range of speaker power fractions. Alternately, FIG. 15C represents the same data with a consistent solenoid pressure of 50 cmH2O. Air pressures 40 cmH2O and 50 cmH2O were chosen because of the performance of the device 10 (FIG. 1) at these pressures in the previous tests (FIGS. 14A-14D). As demonstrated by FIGS. 15B-15C, the reduction in speaker power typically results in an increase in time to penetration. However, any reduction in power between 40% and 80% typically produces penetration at quicker times than one would achieve in conditions without acoustic aid, where penetration occurs after a significantly longer amount of time or does not occur at all. This range of speaker power allows for the variability of speaker power in several different scenarios requiring different sound levels.

Referring now to FIGS. 16A-16D and FIGS. 17A-17D, the effect of tube length on the removal of a secretion blockage is portrayed. Within the graphs, the triangle plot points represent the time it took for penetration using a tube half the length of the full-length tube used in prior experiments, while the circle plot points represent the time it took for penetration using a full-length tube. Specifically, FIGS. 16A-16D test the effect of tube length over varying speaker power fractions, with consistent solenoid frequencies and at consistent speaker frequencies with an air pressure of 40 cmH2O. Further, FIGS. 17A-17D also tests the effect of tube length over varying speaker power fractions with consistent solenoid frequencies and at consistent speaker frequencies, but with an air pressure of 50 cmH2O. Many of the tests showed little to no discrepancy between the half-length tube and the full-length tube, while others showed a switch between the half-length tube and the full-length tube in terms of the length of time to penetration. It is possible to draw the conclusion, therefore, that the length of the tube has little to no effect on the time it takes the device 10 (FIG. 1) to reach penetration of the secretion blockage, making device 10 (FIG. 1) suitable for use in both children and adults.

Figure 18A:
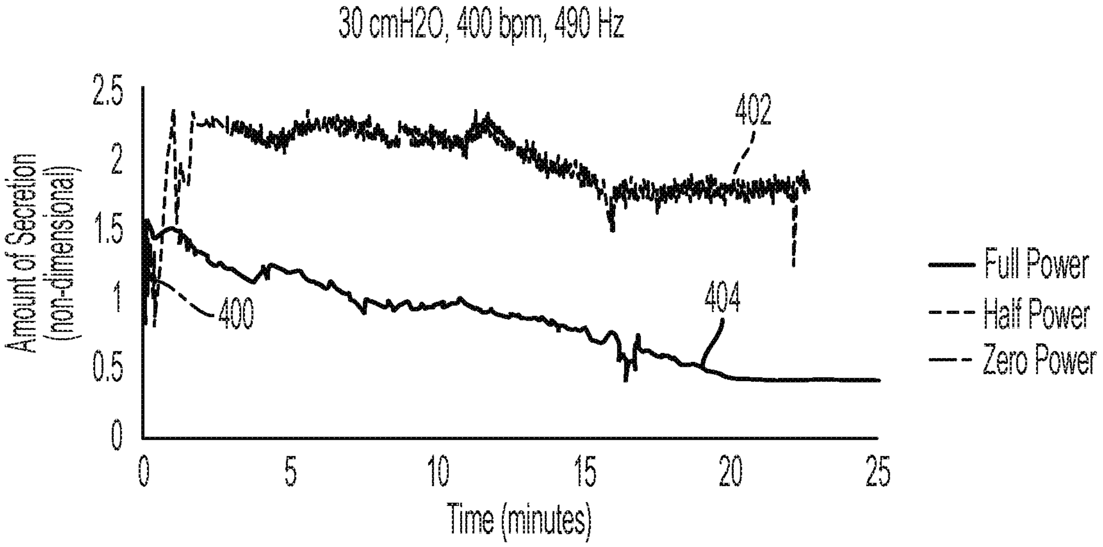
FIG. 18A is a graph illustrating results obtained for removing a blockage or plug of simulated secretion from a simulated airway using a solenoid frequency of 400 bpm, a speaker frequency of 490 Hz, and an air pressure of 30 cmH2O over time at full speaker power, half speaker power, and zero speaker power.
Figure 18B:
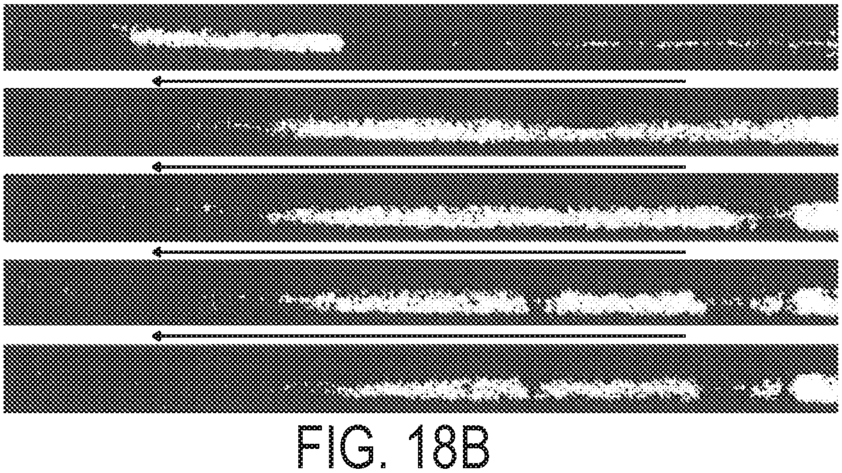
FIG. 18B is a pixelated snapshot of the secretion removal results of FIG. 18A using half speaker power.
Figure 18C:
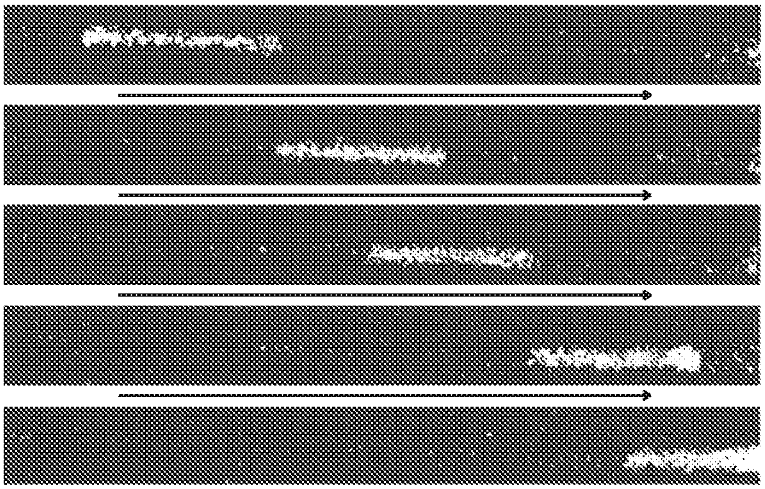
FIG. 18C is a pixelated snapshot of the secretion removal results of FIG. 18A using zero speaker power.

Data from secretion clearance tests can be seen in FIGS. 18A-18C and 19A-19B. Specifically, FIGS. 18A-18C display the amount of secretion over time at a solenoid frequency of 400 bpm, a speaker frequency of 490 Hz, and an air pressure of 30 cmH2O. FIG. 18A compares the test results using full speaker power (104 dB), half speaker power (52 dB), and zero speaker power. Pixelated snapshots of the 52 dB case can be seen in FIG. 18B, while pixelated snapshots of the zero power case are shown in FIG. 18C. In the cases of the pixelated snapshots here and below, the video data is line of sight data, meaning if the secretion is smeared across the test section, the video will not see anything behind it and assume the test section is completely full. Therefore, there is an increase in secretion simulant at the start of every test as the secretion is being penetrated and smeared across the inner wall of the tube. The left side of each snapshot is the mouth side, while the lung side is on the right side of the image, with timing moving forward from top to bottom. As demonstrated by FIG. 18C, the test section with no acoustic enhancement, the secretion simulant is never penetrated and is simply pushed into the artificial lung used for testing.

Figure 19A:
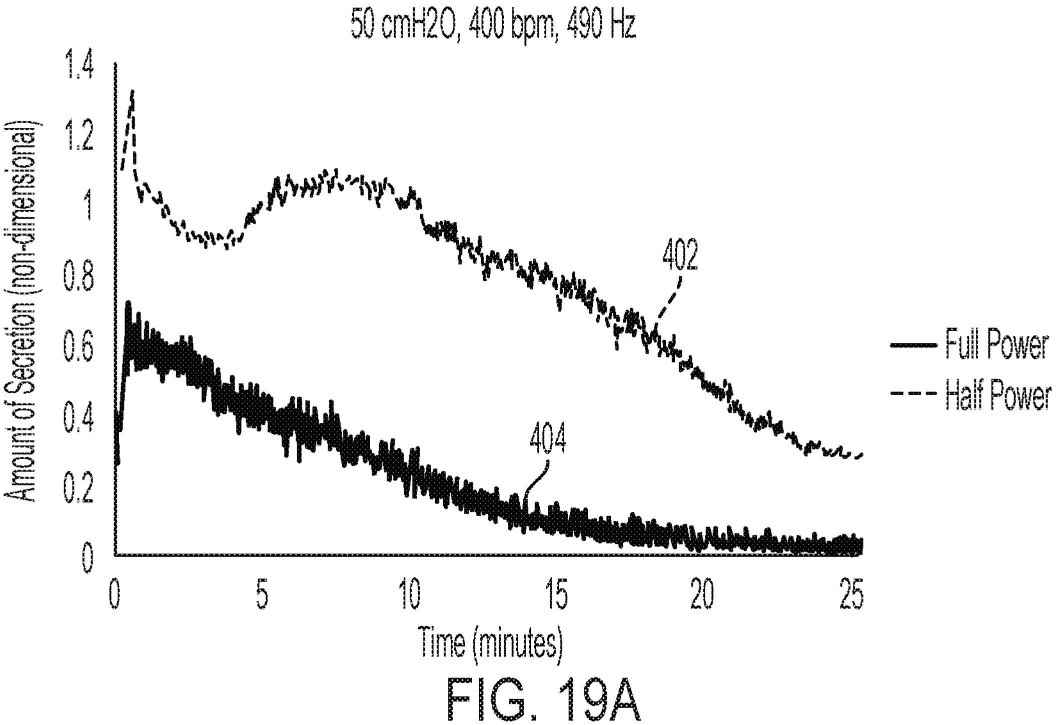
FIG. 19A is a graph illustrating results obtained for removing a blockage or plug of simulated secretion from a simulated airway using a solenoid frequency of 400 bpm, a speaker frequency of 490 Hz, and an air pressure of 50 cmH2O over time at full speaker power and half speaker power.
Figure 19B:
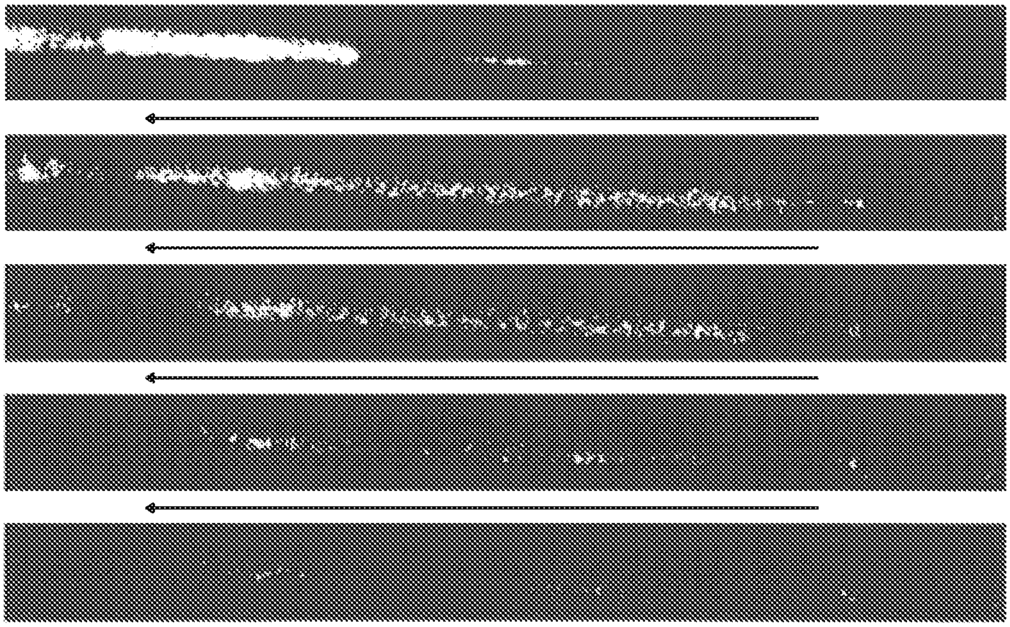
FIG. 19B is a pixelated snapshot of the secretion removal results of FIG. 19A using half speaker power.

FIG. 19A demonstrates the amount of secretion within the simulated airway over time at both half and full power with a solenoid frequency of 400 bpm, a speaker frequency of 490 Hz, and an air pressure of 50 cmH2O. Pixelated snapshots of the half power case can be seen in FIG. 19B.

Figure 20A:
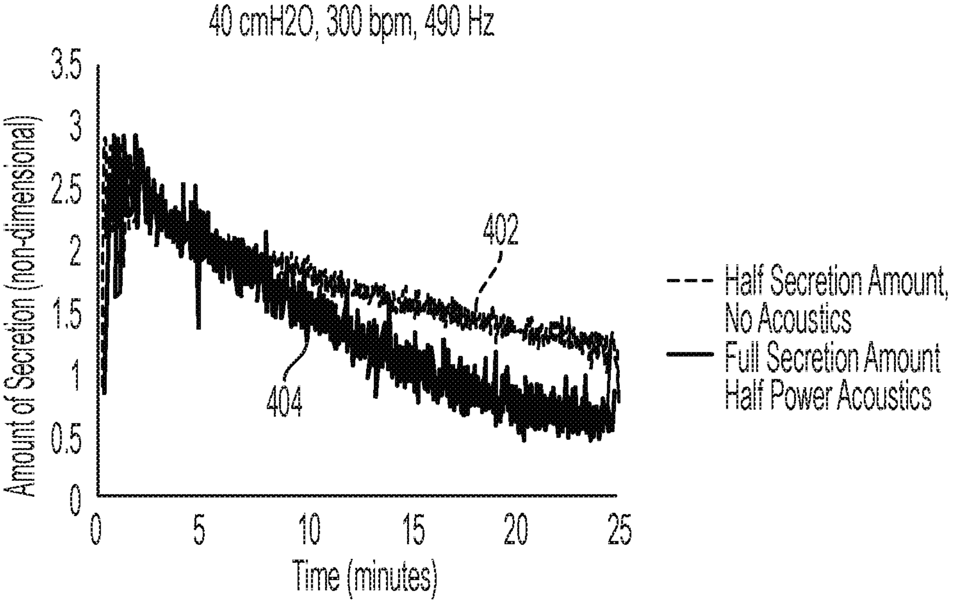
FIG. 20A is a graph illustrating results obtained for removing a blockage or plug of simulated secretion from a simulated airway using a solenoid frequency of 300 bpm, a speaker frequency of 490 Hz, and an air pressure of 40 cmH2O over time at half speaker power with full secretion amount and zero speaker power with half secretion amount.
Figure 20B:
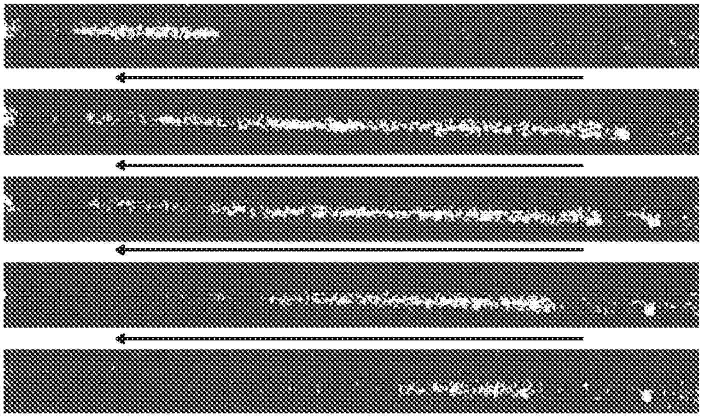
FIG. 20B is a pixelated snapshot of the secretion removal results of FIG. 20A using half speaker power with full secretion amount.
Figure 20C:
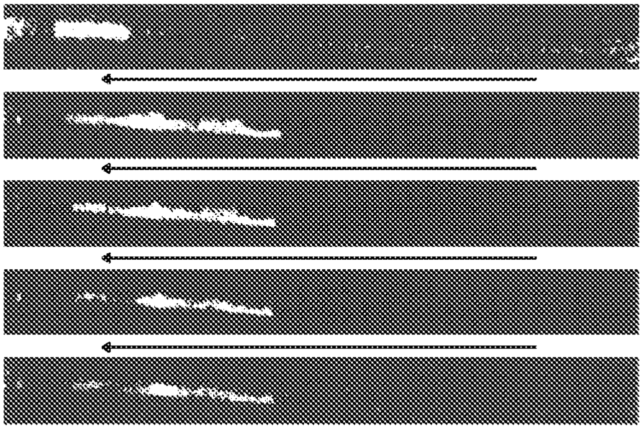
FIG. 20C is a pixelated snapshot of the secretion removal results of FIG. 20A using zero speaker power with half secretion amount.

Now referring to FIGS. 20A-20C, a comparison in the amount of secretion that may be removed from an airway between device 10 (FIG. 1) and a standard IPV without acoustic enhancement is portrayed. A consistent speaker frequency of 490 Hz is used, along with a consistent solenoid frequency of 300 bpm and a consistent air pressure of 40 cmH2O. Specifically, FIG. 20A demonstrates the amount of secretion left in a simulated airway over time using a standard IPV with no acoustic enhancement and using half the initial secretion amount compared to the amount of secretion left in a simulated airway over time using device 10 (FIG. 1) with half power acoustics and using the full secretion amount. FIG. 20B provides the pixelated snapshots of the half power case, while FIG. 20C provides the pixelated snapshots of the zero power case. As demonstrated, the acoustic enhancement allows penetration of twice the amount of secretion in nearly the same amount of time as the standard IPV and is also able to remove the secretion in a shorter amount of time than the standard IPV.

Figure 21A:
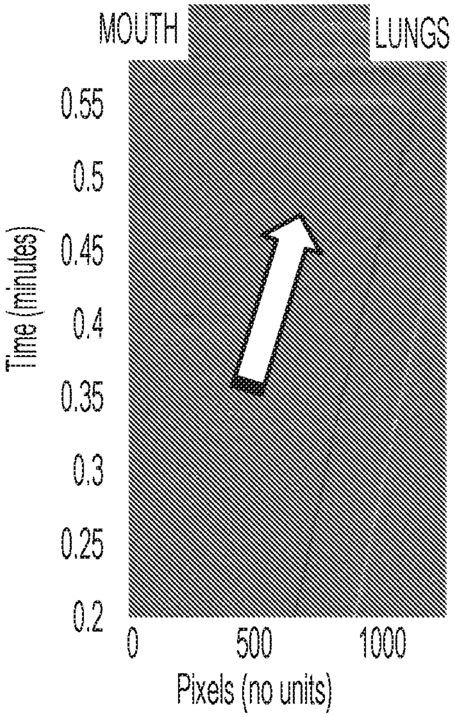
FIG. 21A is a pixelated snapshot illustrating results obtained for removing a blockage of simulated secretion from a simulated airway using a solenoid frequency of 400 bpm and an air pressure of 50 cmH2O with no acoustic enhancement.
Figure 21B:
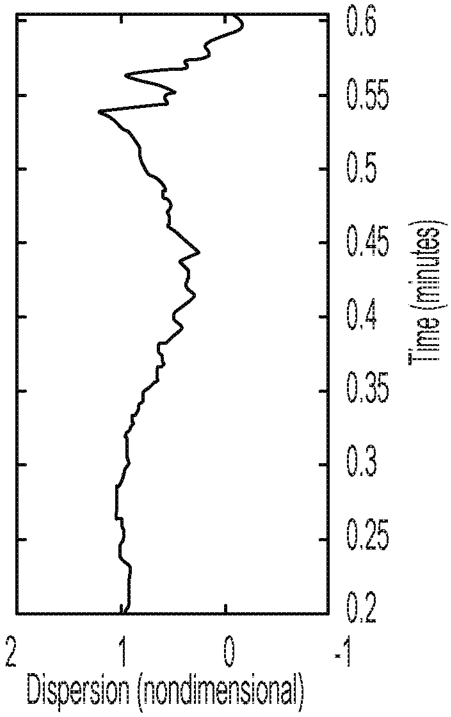
FIG. 21B is a graph illustrating the results of FIG. 21A.

Referring now to FIGS. 21A and 21B, the time to removal of a simulated secretion from a simulated airway is portrayed without the use of acoustic enhancement. A consistent solenoid frequency of 400 bpm is used, along with a consistent air pressure of 50 cmH2O. Specifically referring to FIG. 21B, the non-dimensionalized dispersion of the simulated blockage is plotted as time progresses for the relevant experiment. The non-dimensional value is defined as the ratio of the number of pixels related to the simulated secretion at a given time to the number of pixels related to the simulated secretion at the beginning of the experiment. For example, a value of "1" represents the beginning of the experiment, where the simulated secretion is undisturbed, while a value of "0" represents the end of the test, where the simulated secretion has been removed. In the event of a purely volumetric movement, the value remains below "1"; in the event of a surface deposition of the simulated secretion within the simulated airway, the value exceeds "1."

Referring now to FIG. 21A, the algorithm used in generating the plots of 21B also produces white pixels as the simulated secretion moves into a region of the simulated airway which was previously clear. Otherwise, black pixels are produced when the simulated secretion leaves a region of the simulated airway which was previously clear. Gray pixels represent spatial regions of the simulated airway that has not undergone any change throughout the experiment. As shown in FIG. 21A, the simulated airway blockage in the test setup without use of acoustic enhancements moves continuously downstream toward the lung and is not penetrated and removed toward the mouth.

Figure 22A:
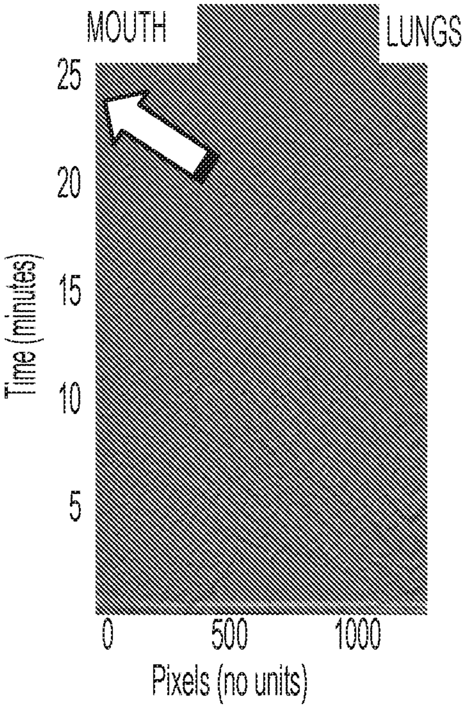
FIG. 22A is a pixelated snapshot illustrating results obtained for removing a blockage of simulated secretion from a simulated airway using a solenoid frequency of 400 bpm and an air pressure of 50 cmH2O with added acoustic enhancement and a speaker frequency of 490 Hz.
Figure 22B:
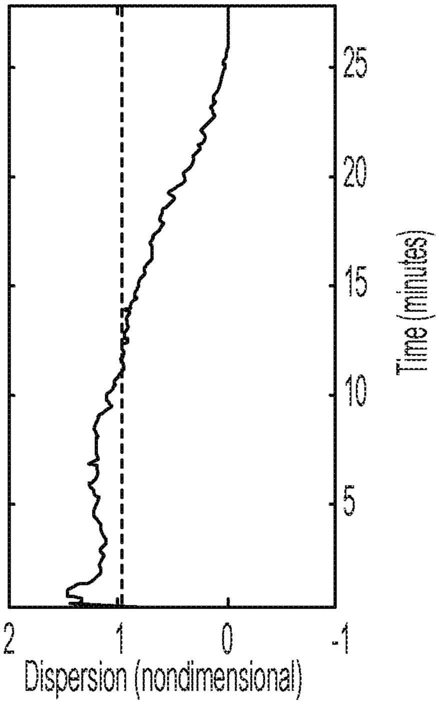
FIG. 22B is a graph illustrating the results of FIG. 22A.

Referring now to FIGS. 22A to 22B, the same experiment described above is reproduced, but additionally uses acoustic enhancement with a speaker frequency of 490 Hz. As shown in FIG. 22A, there is an initial downstream motion of the blockage with considerable surface deposition, relating in penetration of the blockage. The acoustic enhancement is then able to break the blockage into much smaller pieces that can then be gradually pulsed upstream, towards the mouth.

As detailed herein, an illustrative device for unblocking and removing secretions from airways provides therapy by applying oscillated air flow and acoustic vibrations according to a preprogrammed protocol that defines frequency, waveform, pressure amplitude, and oscillation duration through software control. The illustrative device includes an air flow system applying oscillated air flow, an acoustic system applying acoustic vibrations, and a controller operably coupled to the air flow system and the acoustic system, the controller configured to match frequencies, amplitudes, duty cycle, and relative phases to a specific patient's geometry and specific secretions.

Although the invention has been described in detail with reference to certain preferred embodiments, variations and modifications exist within the spirit and scope of the invention as described and defined in the following claims.

What is claimed is:

1. A device for unblocking and removing secretions from an airway, the device comprising:

an air flow system including an air supply, an electrically operable flow control valve in fluid communication with the air supply, and a flow controller in electrical communication with the flow control valve;

an acoustic system operably coupled to the air flow system, the acoustic system including an acoustic pulse generator and an acoustic controller in electrical communication with the pulse generator;

an air flow pathway in fluid communication with the air flow system and in acoustic communication with the acoustic system, the air flow pathway positioned downstream from the air flow system and the acoustic system, the airflow pathway positioned upstream from an outlet;

wherein the acoustic pulse generator is positioned downstream from the flow control valve;

wherein the flow controller causes the flow control valve and the air supply to provide oscillated air flow to the air flow pathway, and the acoustic controller causes the acoustic pulse generator to provide acoustic vibrations to the oscillated air flow;

wherein a defined air flow frequency is between 195 beats per minute and 405 beats per minute;

wherein a defined acoustic vibration frequency is between 295 Hertz and 500 Hertz;

wherein a defined air flow amplitude is between 15 cmH2O and 55 cmH2O; and wherein a defined acoustic vibration amplitude is between 47 decibels and 109 decibels; and wherein the electrically operable flow control valve comprises a solenoid valve.

2. The device of claim 1, wherein the flow controller includes a processor and a memory, the memory including software executed by the processor for defining the oscillated air flow at the defined air flow frequency and the defined air flow amplitude.

3. The device of claim 1, wherein the acoustic controller includes a processor and a memory including software executed by the processor for defining the acoustic vibrations at the defined acoustic vibration frequency and the defined acoustic vibration amplitude.

4. The device of claim 1, wherein an intrapulmonary percussive ventilator defines the flow controller and the flow control valve.

5. The device of claim 1, wherein the pulse generator includes an acoustic speaker and a speaker amplifier.

6. The device of claim 1, further comprising a patient interface in fluid communication with the air flow pathway.

7. The device of claim 1, further comprising a graphical user interface operably coupled to the flow controller and the acoustic controller.

8. The device of claim 1, further comprising a rechargeable battery in electrical communication with the air flow system and the acoustic system.

9. The device of claim 1, wherein a main controller defines the flow controller and the acoustic controller, the main controller including a processor and a memory operably coupled to the processor.

10. The device of claim 9, further comprising a pressure sensor operably coupled to the air flow pathway and in communication with the main controller, the main controller configured to control the air flow system and the acoustic system in response to air pressure detected by the pressure sensor.

11. The device of claim 1, wherein the outlet is configured to be fluidly coupled to a lung.

12. The device of claim 11, wherein the outlet comprises a mouthpiece.

13. A device for unblocking and removing secretions from an airway, the device comprising:

an air flow pathway positioned upstream from an outlet;

an air flow system in communication with the air flow pathway, the air flow system including an air supply, and an electrically operable flow control valve in fluid communication with the air supply;

an acoustic system in communication with the air flow pathway, the acoustic system including a pulse generator configured to generate vibrations;

wherein the air flow pathway is positioned downstream from the air flow system and the acoustic system;

wherein the pulse generator is positioned downstream from the flow control valve;

a main controller is operably coupled to the air flow system and the acoustic system, the main controller configured to control at least one of frequency, waveform, pressure amplitude, and oscillation duration of air provided by the flow control valve, and the main controller configured to control at least one of frequency, amplitude, duty cycle, and relative phase of the vibrations generated by the pulse generator;

wherein the main controller is defined by a flow controller and an acoustic controller, the flow controller in electrical communication with the flow control valve, and the acoustic controller in electrical communication with the pulse generator;

wherein the main controller includes a processor and a memory operably coupled to the processor, and software stored within the memory is executed by the processor for defining air flow at a defined air flow frequency and amplitude, and for defining acoustic vibrations at a defined acoustic vibration frequency and amplitude; and wherein the electrically operable flow control valve comprises a solenoid valve.

14. The device of claim 13, wherein the defined air flow frequency is between 195 beats per minute and 405 beats per minute.

15. The device of claim 13, wherein the defined air flow amplitude is between 15 cmH2O and 55 cmH2O.

16. The device of claim 13, wherein the defined acoustic vibration frequency is between 295 Hertz and 500 Hertz.

17. The device of claim 13, wherein the defined air flow frequency is between 195 beats per minute and 405 beats per minute; the defined air flow amplitude is between 15 cmH2O and 55 cmH2O; the defined acoustic vibration frequency is between 295 Hertz and 500 Hertz; and the defined acoustic vibration amplitude is between 47 decibels and 109 decibels.

18. The device of claim 17, wherein the defined air flow frequency is between 295 beats per minute and 405 beats per minute; the defined air flow amplitude is between 35 cmH2O and 45 cmH2O; the defined acoustic vibration frequency is between 395 Hertz and 405 Hertz; and the defined acoustic vibration amplitude is between 99 decibels and 109 decibels.

19. The device of claim 17, wherein the defined air flow frequency is between 295 beats per minute and 305 beats per minute; the defined air flow amplitude is between 35 cmH2O and 45 cmH2O; the defined acoustic vibration frequency is between 295 Hertz and 305 Hertz; and the defined acoustic vibration amplitude is between 47 decibels and 57 decibels.

20. The device of claim 17, wherein the defined air flow frequency is between 295 beats per minute and 305 beats per minute; the defined air flow amplitude is between 45 cmH2O and 55 cmH2O; the defined acoustic vibration frequency is between 295 Hertz and 405 Hertz; and the defined acoustic vibration amplitude is between 99 decibels and 109 decibels.

21. The device of claim 17, wherein the defined air flow frequency is between 395 beats per minute and 405 beats per minute; the defined air flow amplitude is between 45 cmH2O and 55 cmH2O; the defined acoustic vibration frequency is between 295 Hertz and 405 Hertz; and the defined acoustic vibration amplitude is between 99 decibels and 109 decibels.

22. The device of claim 17, wherein the defined air flow frequency is between 395 beats per minute and 405 beats per minute; the defined air flow amplitude is between 25 cmH2O and 55 cmH2O; the defined acoustic vibration frequency is between 485 Hertz and 495 Hertz; and the defined acoustic vibration amplitude is between 99 decibels and 109 decibels.

23. The device of claim 17, wherein the defined air flow frequency is between 295 beats per minute and 305 beats per minute; the defined air flow amplitude is between 35 cmH2O and 45 cmH2O; the defined acoustic vibration frequency is between 485 Hertz and 495 Hertz; and the defined acoustic vibration amplitude is between 99 decibels and 109 decibels.

24. The device of claim 13, wherein an intrapulmonary percussive ventilator defines the flow controller and the flow control valve.

25. The device of claim 13, wherein the pulse generator includes an acoustic speaker and a speaker amplifier.

26. The device of claim 13, further comprising a patient interface in fluid communication with the air flow pathway.

27. The device of claim 13, further comprising a graphical user interface operably coupled to the flow controller and the acoustic controller.

28. The device of claim 13, further comprising a pressure sensor operably coupled to the air flow pathway and in communication with the controller, the controller configured to adjust at least one of air flow frequency, air flow amplitude, acoustic vibration frequency and acoustic vibration amplitude in response to air pressure detected by the pressure sensor.

29. The device of claim 13, wherein the outlet is configured to be fluidly coupled to a lung.

30. The device of claim 29, wherein the outlet comprises a mouthpiece.

31. A method of unblocking and removing secretions from airways, the method comprising the steps of:

applying oscillated air flow to an air flow pathway including a secretion;

applying acoustic vibrations to the air flow within the air flow pathway;

wherein a defined oscillated air flow frequency is between 195 beats per minute and 405 beats per minute;

wherein a defined air flow pressure amplitude is between 15 cmH2O and 55 cmH2O;

wherein a defined acoustic vibration frequency is between 295 Hertz and 500 Hertz;

wherein a defined acoustic vibration amplitude is between 47 decibels and 109 decibels;

wherein the step of applying oscillated air flow includes the steps of providing an air flow system including an air supply, an electrically operable flow control valve in fluid communication with the air supply, and a flow controller in electrical communication with the flow control valve;

wherein the step of applying acoustic vibrations includes the steps of providing an acoustic system including an acoustic pulse generator and an acoustic controller in electrical communication with the pulse generator;

wherein the acoustic pulse generator is positioned downstream from the flow control valve; and wherein a pressure downstream from the secretion is higher than a pressure upstream from the secretion thereby causing the secretion to move upstream in the air flow pathway.

32. The method of claim 31, wherein the oscillated air flow is controlled by preprogrammed executable instructions that define at least one of frequency, waveform, pressure amplitude, and oscillation duration.

33. The method of claim 31, wherein the acoustic vibrations are controlled by preprogrammed executable instructions that define at least one of frequency, amplitude, duty cycle, and relative phases.

34. The method of claim 31, further comprising the steps of measuring air pressure within the air flow pathway and adjusting the oscillated air flow and acoustic vibrations in response to the measured air pressure.

35. A device for unblocking and removing secretions from an airway, the device comprising:

an air flow system including an air supply, an electrically operable flow control valve in fluid communication with the air supply, and a flow controller in electrical communication with the flow control valve;

an acoustic system operably coupled to the air flow system, the acoustic system including an acoustic pulse generator and an acoustic controller in electrical communication with the pulse generator;

an air flow pathway in fluid communication with the air flow system and in acoustic communication with the acoustic system;

wherein the flow controller causes the flow control valve and the air supply to provide oscillated air flow to the air flow pathway, and the acoustic controller causes the acoustic pulse generator to provide acoustic vibrations to the oscillated air flow, the air flow pathway being positioned downstream from the air flow system and the acoustic system, the air flow pathway being positioned upstream from an outlet;

wherein the acoustic pulse generator is positioned downstream from the flow control valve;

wherein a defined air flow frequency is between 195 beats per minute and 405 beats per minute;

wherein a defined acoustic vibration frequency is between 295 Hertz and 500 Hertz;

wherein a defined air flow amplitude is between 15 cmH2O and 55 cmH2O;

wherein a defined acoustic vibration amplitude is between 47 decibels and 109 decibels wherein the pulse generator includes an acoustic speaker and a speaker amplifier;

wherein a main controller defines the flow controller and the acoustic controller, the main controller including a processor and a memory operably coupled to the processor; and a pressure sensor operably coupled to the air flow pathway and in communication with the main controller, the main controller configured to control the air flow system and the acoustic system in response to air pressure detected by the pressure sensor.

36. The device of claim 35, wherein the outlet is configured to be fluidly coupled to a lung.

37. The device of claim 36, wherein the outlet comprises a mouthpiece.

* * * * *